(12) United States Patent
Tai et al.

(10) Patent No.: US 8,764,708 B2
(45) Date of Patent: Jul. 1, 2014

(54) MEMS DEVICE AND METHOD FOR DELIVERY OF THERAPEUTIC AGENTS

(75) Inventors: Yu-Chong Tai, Pasadena, CA (US); Mark Humayun, Glendale, CA (US); Jason Shih, Yorba Linda, CA (US)

(73) Assignee: The University of Southern California, Los Angeles ( * ) Notice: Subject to any disclaimer, the term of this patent is extended or adjusted under 35 U.S.C. 154(b) by 0 days.

(21) Appl. No.: 13/493,611

(22) Filed: Jun. 11, 2012

(65) Prior Publication Data

US 2013/0000119 A1 Jan. 3, 2013

Related U.S. Application Data

(63) Continuation of application No. 12/790,240, filed on May 28, 2010, now Pat. No. 8,308,686, which is a continuation of application No. 11/686,310, filed on Mar. 14, 2007, now Pat. No. 7,887,508.

(60) Provisional application No. 60/781,969, filed on Mar. 14, 2006.

(51) Int. Cl.
*A61F 7/12* (2006.01)
*B23P 15/00* (2006.01)

(52) U.S. Cl.
USPC ........................................ 604/114; 29/888.02

(58) Field of Classification Search
USPC ............................................................ 604/114
See application file for complete search history.

(56) References Cited

U.S. PATENT DOCUMENTS

| | | |
|---|---|---|
| 3,731,681 A | 5/1973 | Blackshear et al. |
| 3,916,899 A | 11/1975 | Theeuwes et al. |
| 3,977,404 A | 8/1976 | Theeuwes |
| 4,164,560 A | 8/1979 | Folkman et al. |
| 4,373,527 A | 2/1983 | Fischell |
| 4,543,088 A | 9/1985 | Bootman et al. |
| 4,553,973 A | 11/1985 | Edgren |
| 4,692,145 A | 9/1987 | Weyant |
| 4,738,657 A | 4/1988 | Hancock et al. |
| 4,751,926 A | 6/1988 | Sasaki |
| 4,760,837 A | 8/1988 | Petit |
| 4,781,675 A | 11/1988 | White |
| 4,781,695 A | 11/1988 | Dalton |
| 4,838,887 A | 6/1989 | Idriss |

(Continued)

FOREIGN PATENT DOCUMENTS

| | | |
|---|---|---|
| DE | 3915708 | 2/1990 |
| DE | 4436540 | 4/1996 |

(Continued)

OTHER PUBLICATIONS

"FDA Approves and Industry First!—The MED-EL Cochlear Implant System in FDA Approved for Use With Magnetic Resonance Imaging (MRI)," PR Newswire, Durham, N.C., Jun. 18, 2003, 3 pages.

(Continued)

*Primary Examiner* — Jason Flick
(74) *Attorney, Agent, or Firm* — Bingham McCutchen LLP

(57) ABSTRACT

Embodiments of an implantable device for delivering a therapeutic agent to a patient include a reservoir configured to contain a liquid comprising the therapeutic agent, and a cannula in fluid communication with the reservoir. The cannula is shaped to facilitate insertion thereof into a patient's eyeball.

24 Claims, 23 Drawing Sheets

(56) References Cited

U.S. PATENT DOCUMENTS

| | | |
|---|---|---|
| 4,853,224 A | 8/1989 | Wong |
| 4,888,176 A | 12/1989 | Langer et al. |
| 4,944,659 A | 7/1990 | Labbe et al. |
| 4,959,217 A | 9/1990 | Sanders et al. |
| 4,969,874 A | 11/1990 | Michel et al. |
| 5,066,276 A | 11/1991 | Wang |
| 5,108,372 A | 4/1992 | Swenson |
| 5,135,498 A | 8/1992 | Kam et al. |
| 5,135,499 A | 8/1992 | Tafani et al. |
| 5,147,647 A | 9/1992 | Darougar et al. |
| 5,164,188 A | 11/1992 | Wong |
| 5,171,213 A | 12/1992 | Price, Jr. |
| 5,178,604 A | 1/1993 | Baerveldt et al. |
| 5,207,227 A | 5/1993 | Powers |
| 5,213,568 A | 5/1993 | Lattin et al. |
| 5,252,192 A | 10/1993 | Ludwig |
| 5,312,357 A | 5/1994 | Buijs et al. |
| 5,318,557 A | 6/1994 | Gross |
| 5,354,264 A | 10/1994 | Bae et al. |
| 5,389,077 A | 2/1995 | Melinyshyn et al. |
| 5,407,441 A | 4/1995 | Greenbaum |
| 5,425,716 A | 6/1995 | Kawasaki et al. |
| 5,443,505 A | 8/1995 | Wong et al. |
| 5,462,739 A | 10/1995 | Dan et al. |
| 5,472,436 A | 12/1995 | Fremstad |
| 5,476,445 A | 12/1995 | Baerveldt et al. |
| 5,478,328 A | 12/1995 | Silverman et al. |
| 5,527,288 A | 6/1996 | Gross et al. |
| 5,616,219 A | 4/1997 | Patterson |
| 5,676,651 A | 10/1997 | Larson et al. |
| 5,704,520 A | 1/1998 | Gross et al. |
| 5,713,857 A | 2/1998 | Grimard et al. |
| 5,725,017 A | 3/1998 | Elsberry et al. |
| 5,725,493 A | 3/1998 | Avery et al. |
| 5,741,275 A | 4/1998 | Wyssmann |
| 5,785,688 A | 7/1998 | Joshi et al. |
| 5,798,115 A | 8/1998 | Santerre et al. |
| 5,800,420 A | 9/1998 | Gross et al. |
| 5,824,072 A | 10/1998 | Wong |
| 5,830,173 A | 11/1998 | Avery et al. |
| 5,836,935 A | 11/1998 | Ashton et al. |
| 5,868,697 A | 2/1999 | Richter et al. |
| 5,904,144 A | 5/1999 | Hammang et al. |
| 5,989,579 A | 11/1999 | Darougar et al. |
| 5,993,374 A | 11/1999 | Kick |
| 6,144,106 A | 11/2000 | Bearinger et al. |
| 6,203,523 B1 | 3/2001 | Haller et al. |
| 6,240,962 B1 | 6/2001 | Tai et al. |
| 6,251,090 B1 | 6/2001 | Avery et al. |
| 6,264,971 B1 | 7/2001 | Darougar et al. |
| 6,281,192 B1 | 8/2001 | Leahy et al. |
| 6,375,972 B1 | 4/2002 | Guo et al. |
| 6,390,791 B1 | 5/2002 | Maillefer et al. |
| 6,408,878 B2 | 6/2002 | Unger et al. |
| 6,416,777 B1 | 7/2002 | Yaacobi |
| 6,458,102 B1 | 10/2002 | Mann et al. |
| 6,520,936 B1* | 2/2003 | Mann ............................ 604/141 |
| 6,527,744 B1 | 3/2003 | Kriesel et al. |
| 6,537,268 B1 | 3/2003 | Gibson et al. |
| 6,589,205 B1 | 7/2003 | Meadows |
| 6,669,950 B2 | 12/2003 | Yaacobi |
| 6,697,694 B2 | 2/2004 | Mogensen |
| 6,699,394 B2 | 3/2004 | Tai et al. |
| 6,713,081 B2 | 3/2004 | Robinson et al. |
| 6,719,750 B2 | 4/2004 | Varner et al. |
| 6,852,097 B1 | 2/2005 | Fulton, III |
| 6,852,106 B2 | 2/2005 | Watson et al. |
| 6,899,137 B2 | 5/2005 | Unger et al. |
| 6,948,918 B2 | 9/2005 | Hansen |
| 6,973,718 B2 | 12/2005 | Sheppard et al. |
| 7,070,577 B1 | 7/2006 | Haller et al. |
| 7,225,683 B2 | 6/2007 | Harnett et al. |
| 7,276,050 B2 | 10/2007 | Franklin |
| 7,351,303 B2 | 4/2008 | Liu et al. |
| 7,429,258 B2 | 9/2008 | Angel et al. |
| 7,470,267 B2 | 12/2008 | Joshi et al. |
| 7,517,440 B2 | 4/2009 | Anex et al. |
| 7,524,304 B2 | 4/2009 | Genosar |
| 7,537,590 B2 | 5/2009 | Santini, Jr. et al. |
| 7,544,190 B2 | 6/2009 | Pickup et al. |
| 7,606,615 B2 | 10/2009 | Makower et al. |
| 7,766,873 B2 | 8/2010 | Moberg et al. |
| 7,867,203 B2 | 1/2011 | Rosenberg et al. |
| 2002/0016569 A1 | 2/2002 | Critchlow |
| 2002/0026176 A1 | 2/2002 | Varner et al. |
| 2002/0103412 A1 | 8/2002 | Trimmer |
| 2002/0156462 A1 | 10/2002 | Stultz |
| 2002/0188282 A1 | 12/2002 | Greenberg |
| 2003/0014014 A1 | 1/2003 | Nitzan |
| 2003/0014036 A1 | 1/2003 | Varner et al. |
| 2003/0064088 A1 | 4/2003 | Carvalho et al. |
| 2003/0069560 A1 | 4/2003 | Adamis et al. |
| 2003/0141618 A1 | 7/2003 | Braithwaite et al. |
| 2004/0028655 A1 | 2/2004 | Nelson et al. |
| 2004/0096410 A1 | 5/2004 | Maley et al. |
| 2004/0100528 A1 | 5/2004 | Howkins et al. |
| 2004/0126253 A1 | 7/2004 | Gray et al. |
| 2004/0143221 A1 | 7/2004 | Shadduck |
| 2004/0175410 A1 | 9/2004 | Ashton et al. |
| 2004/0199130 A1 | 10/2004 | Chornenky et al. |
| 2004/0208910 A1 | 10/2004 | Ashton et al. |
| 2004/0228734 A1 | 11/2004 | Jeon et al. |
| 2005/0010175 A1 | 1/2005 | Beedon |
| 2005/0065500 A1* | 3/2005 | Couvillon et al. ......... 604/891.1 |
| 2005/0076242 A1 | 4/2005 | Breuer |
| 2005/0096707 A1 | 5/2005 | Hill et al. |
| 2005/0106225 A1* | 5/2005 | Massengale et al. ......... 424/448 |
| 2005/0175708 A1 | 8/2005 | Carrasquillo et al. |
| 2005/0187515 A1 | 8/2005 | Varrichio et al. |
| 2005/0208103 A1 | 9/2005 | Adamis et al. |
| 2005/0214129 A1 | 9/2005 | Greene et al. |
| 2006/0012280 A1 | 1/2006 | Kang et al. |
| 2006/0047538 A1 | 3/2006 | Condurso et al. |
| 2006/0116641 A1 | 6/2006 | Gordon et al. |
| 2006/0167435 A1* | 7/2006 | Adamis et al. ................. 604/500 |
| 2006/0178655 A1* | 8/2006 | Santini et al. ............. 604/891.1 |
| 2006/0200097 A1 | 9/2006 | Humayun et al. |
| 2006/0258994 A1 | 11/2006 | Avery |
| 2006/0259015 A1 | 11/2006 | Steinbach |
| 2006/0271020 A1 | 11/2006 | Huang et al. |
| 2007/0021735 A1 | 1/2007 | Bhavaraju et al. |
| 2007/0060870 A1 | 3/2007 | Tolle et al. |
| 2007/0066939 A1 | 3/2007 | Krulevitch et al. |
| 2007/0084765 A1 | 4/2007 | Tse |
| 2007/0106218 A1 | 5/2007 | Yodfat et al. |
| 2007/0106557 A1 | 5/2007 | Varghese |
| 2007/0112328 A1 | 5/2007 | Steinbach et al. |
| 2007/0118066 A1 | 5/2007 | Pinchuk et al. |
| 2007/0173900 A1 | 7/2007 | Siegel et al. |
| 2007/0191770 A1 | 8/2007 | Moberg et al. |
| 2007/0228071 A1 | 10/2007 | Kamen et al. |
| 2007/0255233 A1 | 11/2007 | Hasse |
| 2007/0255235 A1 | 11/2007 | Olsen et al. |
| 2007/0255250 A1 | 11/2007 | Moberg et al. |
| 2007/0255261 A1 | 11/2007 | Haase |
| 2007/0269487 A1 | 11/2007 | de Juan et al. |
| 2007/0275384 A1 | 11/2007 | Leppert et al. |
| 2008/0015494 A1 | 1/2008 | Santini et al. |
| 2008/0033255 A1 | 2/2008 | Essenpreis et al. |
| 2008/0039768 A1 | 2/2008 | Francis |
| 2008/0039792 A1 | 2/2008 | Meng et al. |
| 2008/0097412 A1 | 4/2008 | Shuros et al. |
| 2008/0119707 A1 | 5/2008 | Stafford |
| 2008/0170936 A1* | 7/2008 | Den Toonder et al. ....... 415/140 |
| 2008/0194053 A1 | 8/2008 | Huang |
| 2008/0243071 A1 | 10/2008 | Quijano et al. |
| 2008/0312584 A1 | 12/2008 | Montgomery et al. |
| 2009/0041624 A1 | 2/2009 | Hochmuth et al. |
| 2009/0112188 A1* | 4/2009 | Santini et al. .............. 604/890.1 |
| 2009/0188576 A1 | 7/2009 | Kang et al. |
| 2009/0192493 A1 | 7/2009 | Meng et al. |
| 2009/0227855 A1 | 9/2009 | Hill et al. |
| 2009/0234594 A1 | 9/2009 | Carlisle et al. |
| 2009/0240215 A1 | 9/2009 | Humayun et al. |

(56) References Cited

U.S. PATENT DOCUMENTS

| | | |
|---|---|---|
| 2009/0259176 A1 | 10/2009 | Yairi |
| 2009/0306585 A1 | 12/2009 | Pang et al. |
| 2009/0306594 A1 | 12/2009 | Pang et al. |
| 2009/0306595 A1 | 12/2009 | Shih et al. |
| 2009/0306633 A1 | 12/2009 | Trovato et al. |
| 2009/0308752 A1 | 12/2009 | Evans et al. |
| 2009/0311133 A1 | 12/2009 | Pang et al. |
| 2009/0312742 A1 | 12/2009 | Pang et al. |
| 2010/0004639 A1 | 1/2010 | Pang et al. |
| 2010/0030550 A1 | 2/2010 | Travieso et al. |
| 2010/0049120 A1 | 2/2010 | Dijksman et al. |
| 2010/0101670 A1 | 4/2010 | Juncker et al. |
| 2010/0143448 A1 | 6/2010 | Nisato et al. |
| 2010/0234805 A1 | 9/2010 | Kaufmann et al. |
| 2010/0241103 A1 | 9/2010 | Kraft et al. |
| 2011/0144586 A1 | 6/2011 | Michaud et al. |
| 2011/0184342 A1 | 7/2011 | Pesach et al. |

FOREIGN PATENT DOCUMENTS

| | | |
|---|---|---|
| DE | 2004-036358 | 2/2006 |
| EP | 251680 | 3/1978 |
| EP | 0209677 | 1/1987 |
| EP | 0251680 | 1/1988 |
| EP | 200646381 | 4/1995 |
| EP | 200815896 | 1/1998 |
| EP | 1649884 | 4/2006 |
| EP | 1841491 | 10/2007 |
| GB | 1345764 | 2/1974 |
| GB | 1452104 | 10/1976 |
| IE | 38474 | 3/1978 |
| WO | WO8401718 | 5/1984 |
| WO | WO8607269 | 12/1986 |
| WO | WO-95/13838 | 5/1995 |
| WO | WO-99/17749 | 4/1999 |
| WO | WO-99/38552 | 8/1999 |
| WO | WO-99/62576 | 12/1999 |
| WO | WO-00/26367 | 5/2000 |
| WO | WO-00/40089 | 7/2000 |
| WO | WO-00/74751 | 12/2000 |
| WO | WO0072900 | 12/2000 |
| WO | WO-01/12158 | 2/2001 |
| WO | WO0126706 | 7/2001 |
| WO | WO-01/56634 | 8/2001 |
| WO | WO-01/66173 | 9/2001 |
| WO | WO-01/94784 | 12/2001 |
| WO | WO 02/067688 A1 | 9/2002 |
| WO | WO-03/002170 | 1/2003 |
| WO | WO03009774 | 2/2003 |
| WO | WO-03/024360 | 3/2003 |
| WO | WO03072193 | 9/2003 |
| WO | WO 2004/002878 A2 | 1/2004 |
| WO | WO-2004/014969 | 2/2004 |
| WO | WO2004026281 | 4/2004 |
| WO | WO-2004/066871 | 8/2004 |
| WO | WO2004067066 | 8/2004 |
| WO | WO-2004/073551 | 9/2004 |
| WO | WO-2005/034814 | 4/2005 |
| WO | WO-2005/046769 | 5/2005 |
| WO | 2006014793 | 2/2006 |
| WO | WO-2006/012280 | 2/2006 |
| WO | WO-2006/014793 | 2/2006 |
| WO | WO2006060586 | 6/2006 |
| WO | 2006075016 | 7/2006 |
| WO | WO-2006/075016 | 7/2006 |
| WO | WO2006121921 | 11/2006 |
| WO | WO2007112328 | 5/2007 |
| WO | WO2007065944 | 6/2007 |
| WO | WO-2007/084765 | 7/2007 |
| WO | WO-2007/106557 | 9/2007 |
| WO | WO2007125456 | 11/2007 |
| WO | WO2007138590 | 12/2007 |
| WO | WO2008024808 | 2/2008 |
| WO | WO2008054788 | 5/2008 |
| WO | WO2008139460 | 11/2008 |
| WO | WO2009015389 | 1/2009 |
| WO | WO2009137780 | 11/2009 |
| WO | WO2011025913 | 3/2011 |
| WO | WO2011028997 | 3/2011 |

OTHER PUBLICATIONS

"Krupin Eye Valve with Scleral Buckle, Krupin Eye Valve With Disk," Hood Laboratories Catalogue, F 079 Rev. Nov. 1992, 4 pages.

"The Optimed Advantage—Glaucoma Pressure Regulator," Optimed Advertising Brochure, Journal of Glaucoma, vol. 2, No. 3, 1993, 4 pages.

Chen et al. "Floating-Disk Parylene Micro Check Valve," Micro Electro Mechanical Systems, 2007, IEEE 20th International Conference on MEMS, Jan. 21-25, 2007, 4 pages.

Chen et al. "Floating-Disk Parylene Microvalve for Self-Regulating Biomedical Flow Controls," IEEE 21st International Conference on MEMS, 2008, Jan. 13-17, 2008, 4 pages.

Chen et al. "Surface-Micromachined Parylene Dual Valves for On-Chip Unpowered Microflow Regulation," Journal of Microelectromechanical Systems, vol. 16, No. 2, Apr. 2007, pp. 223-231.

Choudhri et al. "A Comparison of Dorzolamide-Timolol Combination Versus the Concomitant Drugs," American Journal of Ophthalmology, Dec. 2000, 130, pp. 832-833.

Eliason et al. "An Ocular Perfusion System," Invest. Ophthalmol. Vis. Sci., vol. 19, No. 1, Jan. 1980, pp. 102-105.

Hashizoe et al. "Scleral Plug of Biodegradable Polymers for Controlled Release in the Vitreous" Arch Ophthalmol, vol. 112, Oct. 1994, pp. 1380-1384.

Jabs "Treatment of Cytomegalovirus Retinitis—1992," Arch Ophthlmol, vol. 110, Feb. 1992, pp. 185-187.

Khouri et al. "Use of Fixed-Dose Combination Drugs for the Treatment of Glaucoma," Drugs Aging, 2007, 24, 12, pp. 1007-1016.

Kimura et al. "A New Vitreal Drug Delivery System Using an Implantable Biodegradable Polymeric Device," Investigative Ophthalmology & Visual Science, May 1994, vol. 35, No. 6; pp. 2815-2819.

Lo et al. "A Refillable Polymer Drug Delivery Device for Treatment of Ocular Diseases," The Royal Society of Chemistry, Jan. 1, 2007, 28 pages.

Michelson et al. "Experimental Endophtalmitis Treated With an Implantable Osmotic Minipump," Arch Ophthalmol, vol. 97, Jul. 1979, pp. 1345-1346.

Miki, et al. "A Method for Chronic Drug Infusion Into the Eye," Japanese Journal of Ophthalmology, vol. 28, 1984, pp. 140-146.

Pincus et al. "Why are Only 50% of Courses of Anti-Tumor Necrosis Factor Agents Continued for Only 2 Years in Some Settings? Need for Longterm Observations in Standard Care to Compliment Clinical Trials," Journal of Rheumatology, 2006, 33, 12, pp. 2372-2375.

Pope et al. "MRI in Patients with High-Grade Gliomas Treated with Bevacizumab and Chemotherapy," Neurology, 2006, 66, pp. 1258-1260.

Rubsamen et al. "Prevention of Experimental Proliferative Vitreoretinopathy With a Biodegradable Intravitreal Implant for the Sustained Release of Fluorouracil," Arch Ophthalmol, vol. 112, Mar. 1994, pp. 407-413.

Sanborn et al. "Sustained-Release Ganciclovir Therapy for Treatment of Cytomegalovirus Retinitis," Arch Ophthmol, vol. 110, Feb. 1992; pp. 188-195.

Smith et al. "Intravitreal Sustained-Release Ganiclovir," Arch Ophthlmol, vol. 110, Feb. 1992, pp. 255-258.

Stark-Vance, "Bevacizumab and CPT-11 in the Treatment of Relapsed Malignant Glioma," Abstract from the World Federation of Neuro-Oncology Second Quadrennial Meeting and Sixth Meeting of the European Association for Neuro-Oncology, May 5-8, 2005, Abstract 342, p. 369.

Steyer "Alcon Eye-Drug Setback Raises the Stakes," The Street. Com, Oct. 14, 2004, 4 pages.

Strohmaier et al. "The Efficacy and Safety of the Dorzolamide-Timolol Combination Versus the Concomitant Administration of its Components," Ophthalmology, Oct. 1998, vol. 105, No. 10, pp. 1936-1944.

(56) References Cited

OTHER PUBLICATIONS

Xie et al. "An Electrochemical Pumping System for On-Chip Gradient Generation," Analytical Chemistry, Jul. 1, 2004, vol. 76, No. 13, pp. 3756-3763.
Examination Report for European Patent Application No. 07753177.0, mailed Jan. 29, 2009, 6 pages.
Invitation to Pay Additional Fees and Partial International Search for PCT Application No. PCT/US2007/006530, mailed Jul. 31, 2007, 7 pages.
International Search Report for PCT Application No. PCT/US2007/006530, mailed Nov. 12, 2007, 7 pages.
Written Opinion for PCT Application No. PCT/US2007/006530, mailed Nov. 12, 2007, 10 pages.
Invitation to Pay Additional Fees and Partial International Search for PCT Application No. PCT/US2009/030019, mailed Jun. 5, 2009, 5 pages.
International Search Report for PCT Application No. PCT/US2009/030019, mailed Jul. 20, 2009, 7 pages.
Written Opinion for PCT Application No. PCT/US2009/030019, mailed Jul. 20, 2009, 9 pages.
Invitation to Pay Additional Fees and Partial International Search for PCT Application No. PCT/US2008/087690, mailed May 15, 2009, 5 pages.
International Search Report for PCT Application No. PCT/US2008/087690, mailed Aug. 11, 2009, 7 pages.
Written Opinion for PCT Application No. PCT/US2008/087690, mailed Aug. 11, 2009, 10 pages.
Invitation to Pay Additional Fees and Partial International Search for PCT Application No. PCT/US2009/043317, mailed Nov. 16, 2009, 5 pages.
Invitation to Pay Additional Fees and Partial International Search for PCT Application No. PCT/US2009/043313, mailed Nov. 16, 2009, 6 pages.
International Search Report for PCT Application No. PCT/US2009/043325, mailed Dec. 11, 2009, 9 pages.
Written Opinion for PCT Application No. PCT/US2009/043325, mailed Dec. 11, 2009, 9 pages.
Examination Report for European Patent Application No. 07753177.0, mailed Feb. 5, 2010, 3 pages.
International Search Report for PCT Application No. PCT/US2009/043317, mailed Feb. 16, 2010, 7 pages.
Written Opinion for PCT Application No. PCT/US2009/043317, mailed Feb. 16, 2010, 8 pages.
International Search Report for PCT Application No. PCT/US2009/043313, mailed Feb. 25, 2010, 8 pages.
Written Opinion for PCT Application No. PCT/US2009/043313, mailed Feb. 25, 2010, 8 pages.
Examination Report mailed Jan. 29, 2009 for European Patent Application No. 07753177.0 (6 pages).
Examination Report mailed Feb. 5, 2010 for European Patent Application No. 07753177.0 (3 pages).
Extended Search Report mailed Dec. 15, 2011 for European Patent Application No. 11153615.7 (9 pages).
Extended Search Report mailed Dec. 12, 2011 for European Patent Application No. 11153618.1 (10 pages).
Office Action mailed Jan. 19, 2012 for Australian Patent Application No. MX/a/2008/011714, 2 pages (translation).
Examination Report mailed Oct. 23, 2012 for European Patent Application No. 1153618.1 (5 pages).
Examination Report mailed Oct. 24, 2012 for European Patent Application No. 11153615.7 (4 pages).

\* cited by examiner

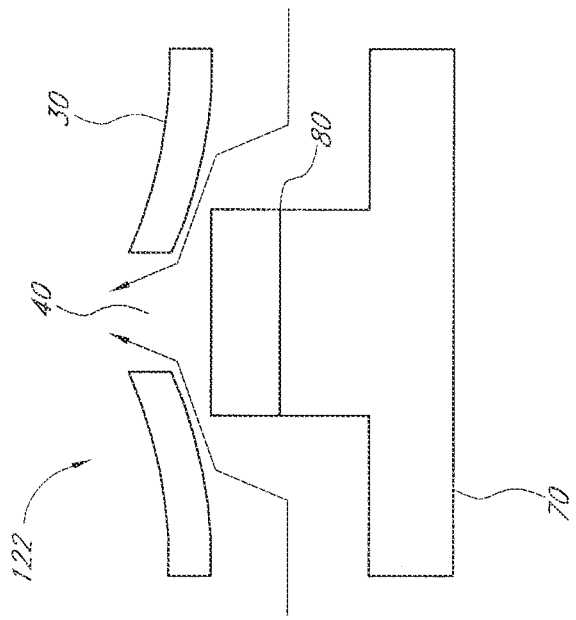
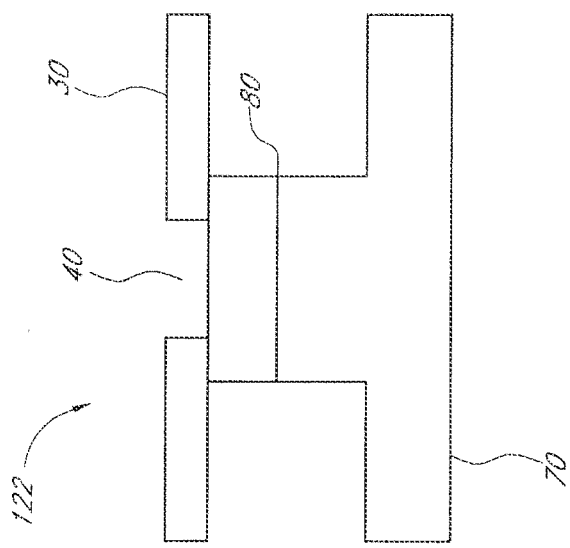

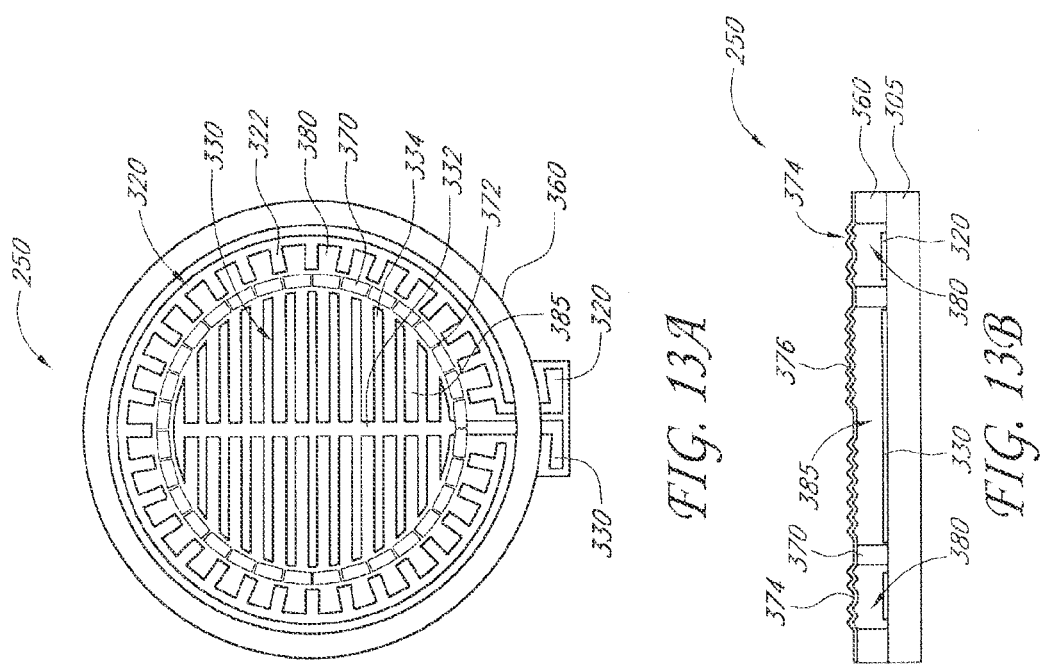

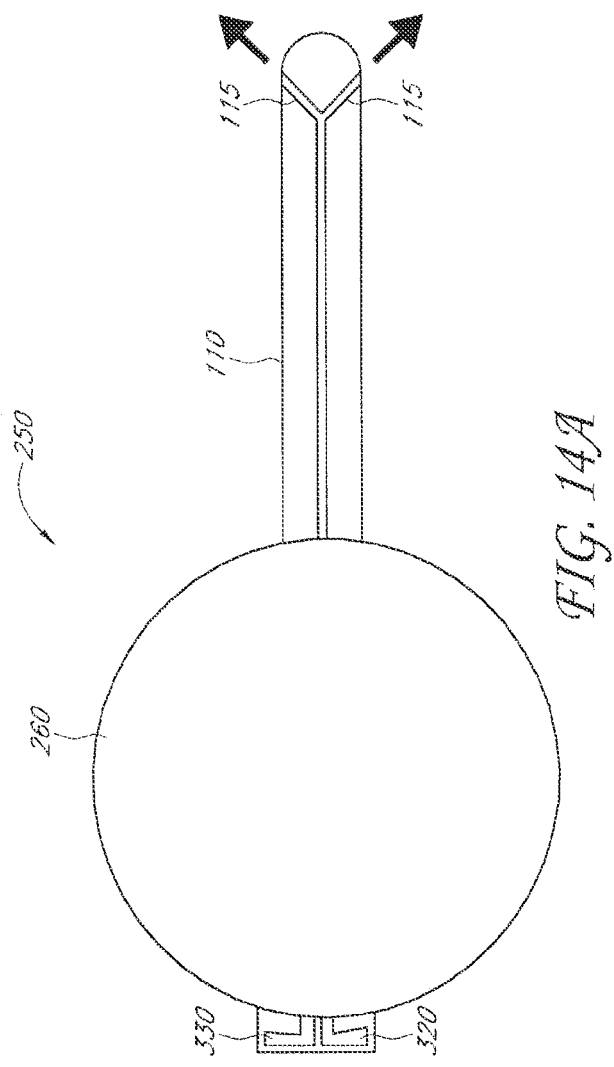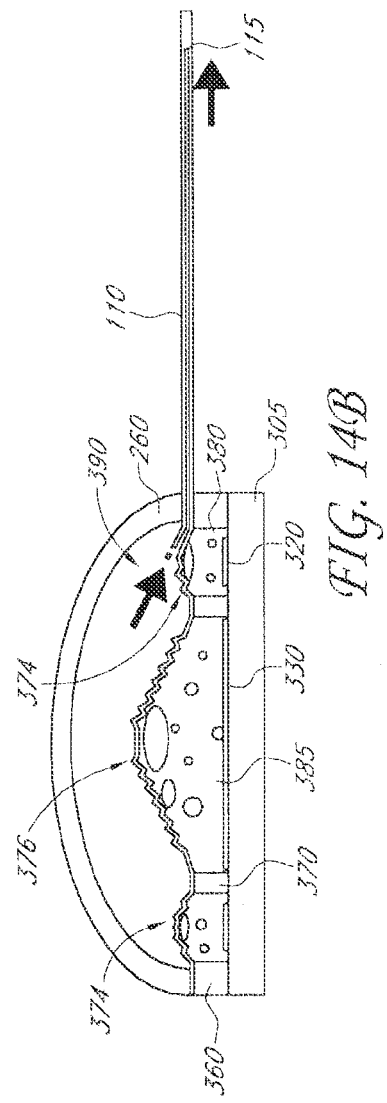
FIG. 14A
FIG. 14B

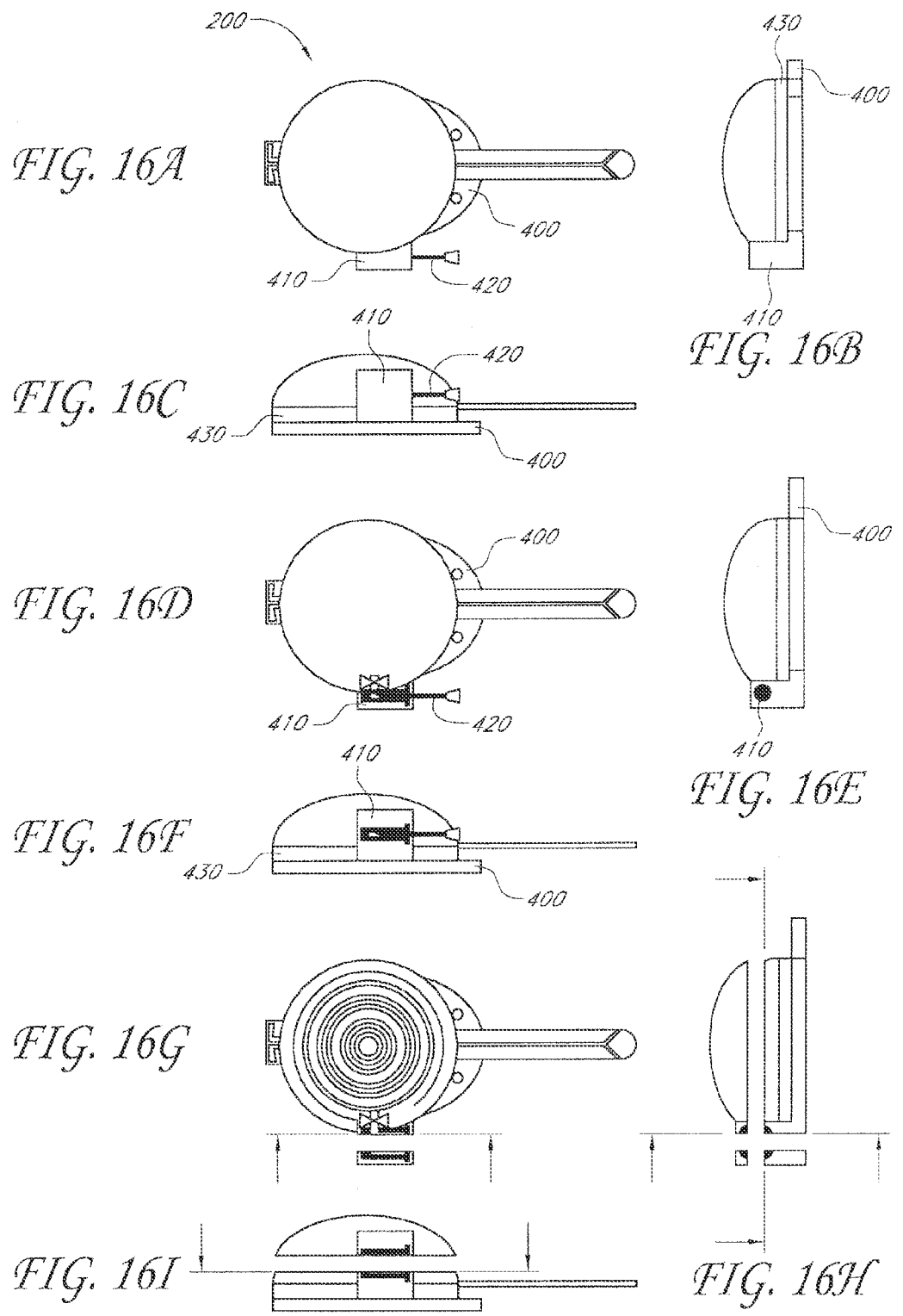

Silicon  Pt/Ti  Roughened Silicon  Cr/Au
Silicon Dioxide  Photoresist  Parylene  SU-8

Flow rate testing

Ultra low flow rate

Pump efficiency

Gas recombination

MEMS DEVICE AND METHOD FOR DELIVERY OF THERAPEUTIC AGENTS

CLAIM OF PRIORITY

This application is a continuation of, claims priority to and the benefit of, and incorporates by reference herein in its entirety, U.S. patent application Ser. No. 12/790,240, which was filed on May 28, 2010, which is a continuation of, U.S. patent application Ser. No. 11/686,310, which was filed on Mar. 14, 2007 and which claimed priority to and the benefit of U.S. Provisional Patent Application No. 60/781,969, filed Mar. 14, 2006, which is also incorporated in its entirety by reference herein.

STATEMENT REGARDING FEDERALLY SPONSORED R&D

Work leading to the invention described herein was supported by the U.S. Government, so the U.S. Government has certain rights to the invention pursuant to Grant No. EEC-0310723 awarded by the National Science Foundation.

BACKGROUND OF THE INVENTION

1. Field of the Invention

This application relates generally to devices and methods for delivery of therapeutic agents to a patient, and more specifically to delivery of therapeutic agents by an implanted device.

2. Description of the Related Art

Medical treatment often requires administration of a therapeutic agent (e.g., medicament, drugs) to a particular part of the body, intravenous injection has long been a mainstay in medical practice to deliver drugs systemically. Some maladies, however, requires administration of drags to anatomical regions or portions to which access is more difficult to achieve.

Eyes are a prime example of anatomical regions in which access is constrained. Ocular pathologies such as diabetic retinopathy and macular degeneration are best treated by administration of drugs to the vitreous humor, which has no fluid communication with the vasculature. Such administration not only delivers drug directly to where it is needed, but also importantly minimizes the exposure of fee rest of the body to the drug and therefore to its inevitable side effects.

Injection into the patient's body (e.g., into the vitreous humor of the eye), white medically feasible, delivers a bolus of drag. Many times, however, administration of a bolus of drug is undesirable. For example, drugs often have concentration-dependent side effects that limit the maximum concentration optimally administered to the body. Certain drags exert their therapeutic action only when their concentration exceeds a threshold value for a given period. For such drugs, the exponential decay in concentration with time of a bolus injection would necessitate repeated injections to maintain the desired drug concentration in fee body. Repeated injections not only entail the expense and inconvenience of repeated office visits, but also the unpleasantness of the injections themselves. In addition, with regard to intraocular treatments, repeated injections increase the risk of damage to the eye through infection, hemorrhage, or retinal detachment.

These problems are particularly severe in the case of chronic ailments that require long-term administration of a drug either for treatment and/or for prophylactic maintenance. Other chronic diseases, such as diabetes, are now treated by devices that gradually deliver therapeutic medicaments over time, avoiding or at least reducing the "sawtooth" pattern associated with repeated administration of boluses.

SUMMARY OF THE INVENTION

In certain embodiments, an implantable device for delivering a therapeutic agent to a patient is provided. The device comprises a reservoir configured to contain a liquid comprising the therapeutic agent. The device further comprises a cannula in fluid communication with the reservoir, the cannula having an outlet configured to be in fluid communication with the patient. The device further comprises a valve comprising a movable element movable between a first position and a second position. The movable element comprises an orifice therethrough, wherein the liquid flows through the orifice to the outlet when the movable element is in the first position and wherein the liquid does not flow through the orifice to the outlet when the movable element is in the second position.

In certain embodiments, an implantable device for delivering a therapeutic agent to a patient is provided. The device comprises a reservoir configured to contain a liquid comprising the therapeutic agent. The device further comprises a cannula in fluid communication with the reservoir. The cannula has an outlet configured to be in fluid communication with the patient. The device further comprises a first electrode and a second electrode, at least one of the first electrode and the second electrode is planar. The device further comprises a material in electrical communication with the first and second electrodes. A voltage applied between the first electrode and the second electrode produces gas from the material, the gas forcing the liquid to flow from the reservoir to the outlet.

In certain embodiments, a method of making an implantable device for delivering a therapeutic agent to a patient is provided. The method comprises forming a plurality of structural layers. The method further comprises bonding the plurality of structural layers together to form a reservoir configured to contain a liquid and a cannula in fluid communication with the reservoir, the cannula having an outlet configured to be in fluid communication with the patient.

In certain embodiments, a method is provided for delivering a therapeutic agent to a patient. The method comprises providing a device implanted in or on a patient. The device comprises a reservoir containing a liquid comprising the therapeutic agent. The device further comprises a cannula in fluid communication with the reservoir, the cannula having an outlet in fluid communication with the patient. The device further comprises a first electrode, a second electrode, and a material in electrical communication with the first and second electrodes. The method further comprises applying a first voltage between the first electrode and the second electrode to produce gas from the material, the gas forcing the liquid to flow from the reservoir to the outlet. The method further comprises applying a second voltage between the first electrode and the second electrode to produce the material from the gas.

BRIEF DESCRIPTION OF THE DRAWINGS

FIGS. 6A and 6B show cross-sectional views of the operation of an example valve compatible with certain embodiments described herein.

FIGS. 13A and 13B schematically illustrate an example electrolysis micropump compatible with certain embodiments described herein.

FIGS. 14A and 14B schematically illustrate top and cut-away side views of an example electrolysis micropump compatible with certain embodiments described herein.

FIG. 15D includes a legend applicable to FIGS. 15A-15D.

FIGS. 16A-16I show various views of an example of a drug delivery system with drug reservoir, cannula, valving, pump, refillable port, and suture labs.

FIG. 19M includes a legend applicable to FIGS. 19A-19M.

DETAILED DESCRIPTION OF THE PREFERRED EMBODIMENT

Figure 1:
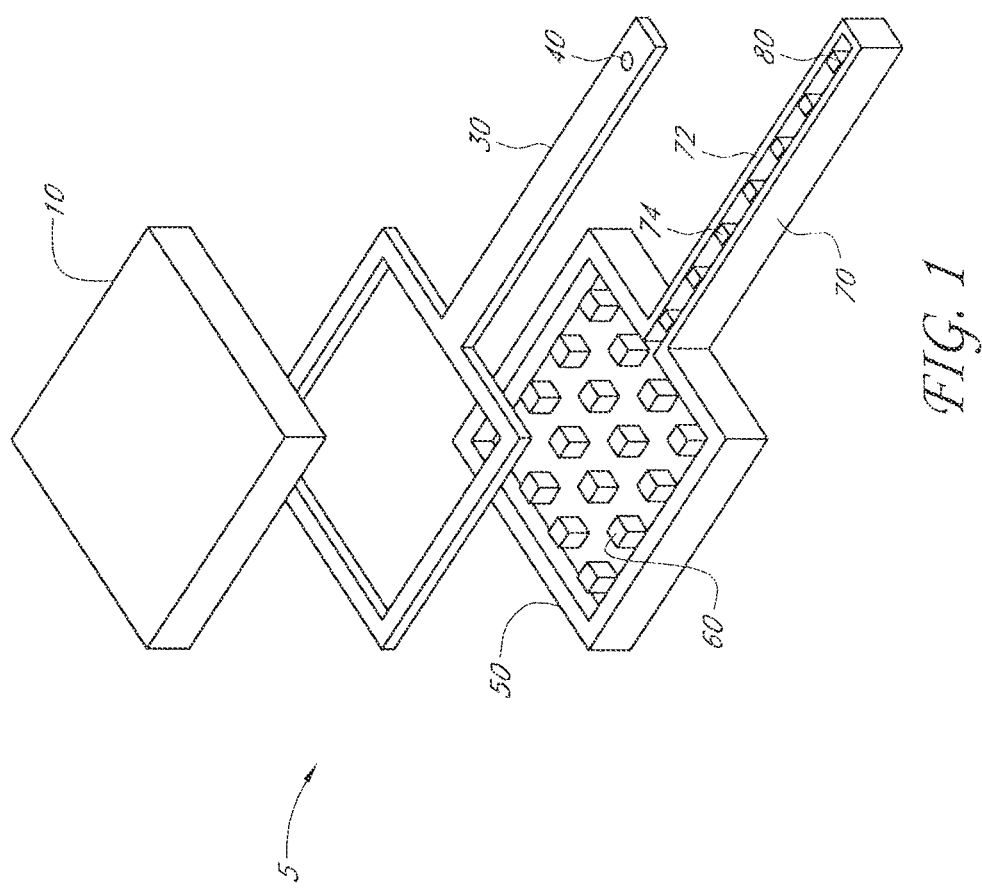
FIG. 1 shows an exploded view of the three layers that form an example drug delivery device compatible with certain embodiments described herein.

Unless otherwise specified, technical terms are used herein to have their broadest meaning to persons skilled in the art, including but not limited to, the meanings specified in the McGraw-Hill Dictionary of Scientific and Technical Terms, $6^{th}$ edition.

In vivo sustained release implants are a new and promising technology. Most utilize minimal surgery to be inserted. There is a trade-off between size and repeated use for these implants. Smaller devices provide comfort but contain a limited amount of drug, thus requiring replacement. Larger devices do not need to be replaced but instead can be refilled. Certain pharmaceutical treatments of chronic eye diseases (e.g., glaucoma) necessitate repeated doses to be delivered to the eye. Such devices are also advantageously small due to the space restrictions of the eye. Therefore, in certain embodiments described herein, drug delivery systems for the eye advantageously combine small size and a refillable reservoir.

Drug delivery devices for the eye have particularly demanding requirements. Clearly, any such device is advantageously made as small as possible to minimize the discomfort of its presence in the eye. On the other hand, the device advantageously holds as much drug as possible, to maximize the time before the drug supply is exhausted and the device must be replaced or refilled. These mutually antithetical requirements greatly complicate the challenge of designing practical implantable devices for delivering drugs within the eye. In addition, some applications, such as administering treatment within the eye, pose even more serious problems. Repeated injections can easily damage delicate ocular tissues, and can result in hemorrhage, infection, and cataracts. In addition, some areas of the body simply cannot be reached by injection.

A need therefore exists for a device for drug delivery to a patient's body for which certain embodiments are small but can deliver a sufficient amount of drug over an extended period without needing to be replaced. Certain embodiments described herein answer this need by providing an implantable drug delivery device that, while small, is refillable, and therefore can supply a fluid, such as a solution of a drag, over extended periods by being refilled in situ rather than replaced. Certain embodiments described herein provide a device with a reservoir that has a self-resealing upper layer feat can be pierced with a needle for refilling, and a lower layer that resists needle punctures and thereby protects the eye from accidental injury during the refilling process.

Certain embodiments described herein provide an implantable intraocular drag delivery system that includes a refillable reservoir, a cannula, and a valve. The refillable reservoir holds the fluid to be delivered, the cannula directs the fluid to the targeted site, and the valve controls when fluid is delivered and prevents backflow. The cannula of certain embodiments is tapered to facilitate its insertion into the eye. In general, the fluid will contain one or more drugs. The term "drug" is used herein to have its broadest meaning to persons skilled in the art, including, bra not limited to, drug substance per se, medicaments, therapeutic agents, and fluids containing such substances.

Figure 2:
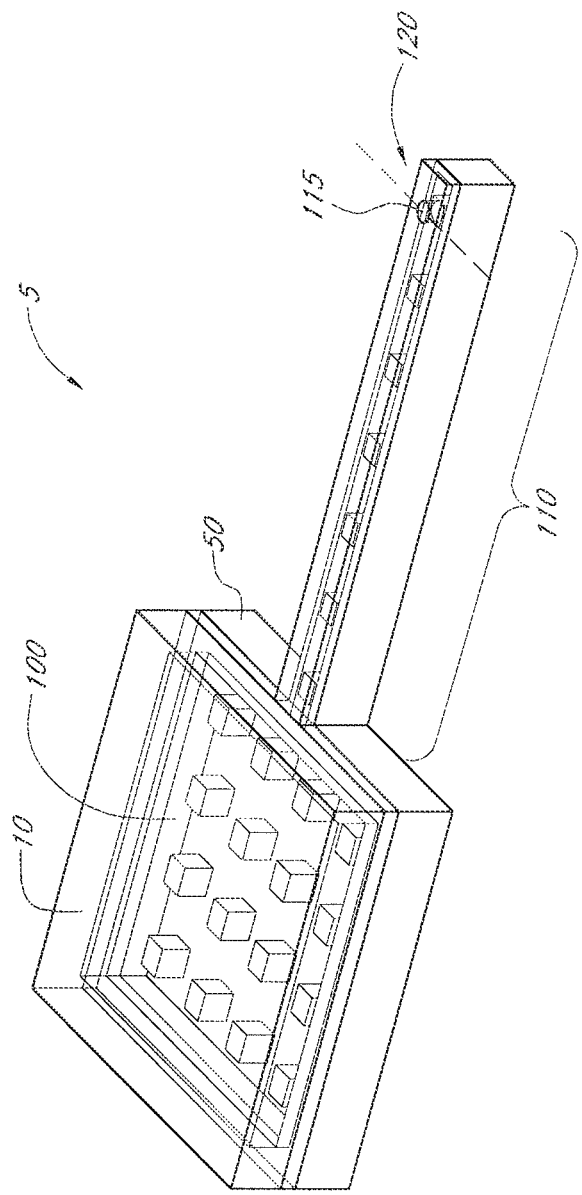
FIG. 2 shows an assembled example drug delivery device compatible with certain embodiments described herein.

FIG. 1 and FIG. 2 schematically illustrate an exploded view and an assembled view, respectively, of an example device 5 compatible with certain embodiments described herein. The device 5 comprises a reservoir 100 configured to contain a liquid comprising a therapeutic agent. The device 5 further comprises a cannula 110 in fluid communication with the reservoir 100. The cannula 110 has an outlet 115 configured to be in fluid communication with the patient. The device 5 further comprises a valve 120 comprising a movable element which is movable between a first position and a second position. The movable element comprises an orifice 40 therethrough. The liquid flows through the orifice 40 to the outlet 115 when the movable element is in the first position. The liquid does not flow through the orifice 40 to the outlet 115 when the movable element is in the second position.

Figure 3:
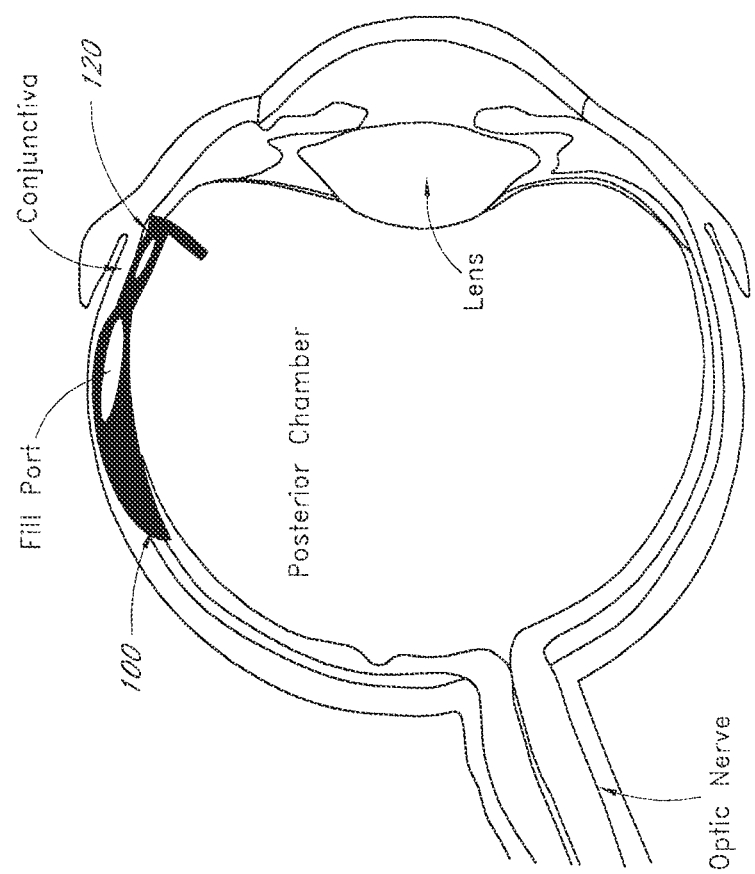
FIG. 3 illustrates an example location for implantation of an example drug delivery device in the eye.

FIG. 3 schematically illustrates an example device 5 implanted in the eye in accordance with certain embodiments described herein. The device 5 of FIG. 3 is placed upon the conjunctiva of the eye and cannula 110 is inserted through to the posterior chamber of the eye. As described more fully below, the reservoir 100 of certain embodiments includes a needle-pierceable portion of a first wall 10 that serves as a fill port for the reservoir 100. The device 5 administers fluid to the posterior chamber through the cannula 110 and the valve 120, which in this embodiment is located at or near the end 117 of the cannula 110 inserted into the posterior chamber. In certain other embodiments, the device 5 can be used to administer fluid to the anterior chamber of the eye, which is separated front the posterior chamber by the lens. In certain other embodiments, the device 5 is implanted in other portions of the body (e.g., in the sub-arachnoid space of the brain for providing chemotherapy or in a pancreas that does not respond well to glucose next to beta cells to provide materials (e.g., proteins, viral vectors) that will trigger insulin release. In certain embodiments, the device 5 is advantageously refutable. In certain such embodiments, the reservoir 100 comprises a first wall 10 which is generally puncturable by a needle (not shown), thereby allowing refilling of the reservoir 100 through the needle. At least a portion of the first wall 10 of certain embodiments comprises a soft plastic material that can be punctured with a needle and which reseats itself upon removal of the needle, thereby providing a self-sealing portion of the first wall 10. The self-sealing material advantageously provides a reservoir refill site that can withstand multiple punctures, and is biocompatible. Examples of such materials compatible with certain embodiments described herein include, but are not limited to, polydimethylsiloxane (PDMS), polycarbonates, polyolefins, polyurethanes, copolymers of acrylonitrile, copolymers of polyvinyl chloride, polyamides, polysulphones, polystyrenes, polyvinyl fluorides, polyvinyl alcohols, polyvinyl esters, polyvinyl butyrate, polyvinyl acetate, polyvinylidene chlorides, polyvinylidene fluorides, polyimides, polyisoprene, polyisobutylene, polybutadiene, polyethylene, polyethers, polytetrafluoroethylene, polychloroethers, polymethylmethacrylate, polybutylmethacrylate, polyvinyl acetate, nylons, cellulose, gelatin, silicone rubbers and porous rubbers.

Figure 4:
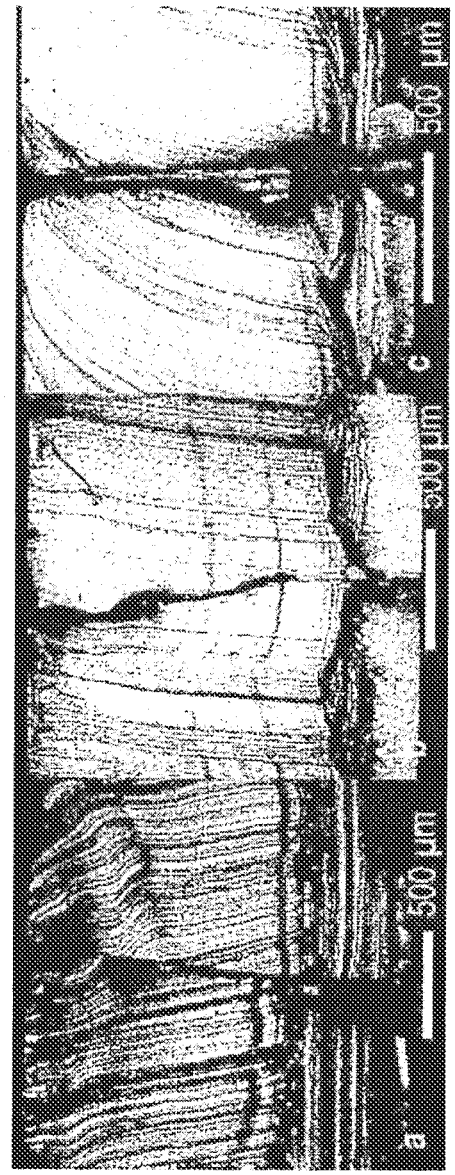
FIG. 4 shows optical microscope images of a cross-sectional view of polydimethylsiloxane after it was punctured using a (a) 20-gauge standard needle, (b) 30-gauge non-coring needle, and (c) 30-gauge coring needle.

FIG. 4 is a series of photomicrographs which illustrate the stability of polydimethylsiloxane (PDMS) as a material for the first wall 10. Three different needle styles were inserted into a slab of PDMS: (i) a 20-gauge non-coring needle, (ii) a 30-gauge non-coring needle, and (iii) a 30-gauge coring needle, and the puncture sites were observed using scanning electron microscopy and optical microscopy. A standard sharp-tipped 20-gauge needle and a 30-gauge non-coring needle allowed the PDMS to self-seal the puncture hole after the needle was removed. However, the 30-gauge coring needle left a channel in the PDMS after it was removed. The puncture mechanism in small diameter needles of either standard or non-coring styles appears to tear and displace the PDMS material rather than removing material, thereby allowing the PDMS to reseal the puncture hole. The structural integrity of the PDMS was observed after multiple punctures with a 25-gauge needle. Table 1 shows the relationship between the wall thickness and leakage for tests performed under atmospheric conditions with leakage determined through visual inspection.

TABLE 1

| Thickness (millimeters) | Number of punctures until failure |
| --- | --- |
| 0.3557 | 1 |
| 0.508 | 7 |
| 0.4826 | 10 |
| 0.4578 | 22 |
| 0.5334 | 21 |

The refillable reservoir 100 of certain embodiments can be used with a variety of drug-containing fluids. In some cases, it may be desirable to remove any remaining fluid from the reservoir 100 before refilling, for example to purge the device 5. In certain such embodiments, the fluid can be changed by removing any remaining fluid from the reservoir by inserting a needle or syringe through the self-sealing portion of the first wall 10 and filling the reservoir 100 with a new drug-containing fluid via a needle or syringe inserted through the self-sealing portion of the first wall 10. Purging, if desired, can be effected through cycles of injection and removal of a purging fluid.

In certain embodiments, refilliability of the reservoir 100 advantageously allows the device 5 to be smaller than it may otherwise be because the reservoir 100 does not have to be sufficiently large to hold a lifetime supply of the drug to be administered. Furthermore, the smaller size of the device 5 advantageously reduces the invasiveness of the device 5 both for implantation and daily use.

In certain embodiments, the refillability of the reservoir 100 advantageously allows the physician to tailor the therapeutic regimen to the patient's changing needs or to take advantages of new advances in medicine. In certain embodiments, the refillable reservoir 100 advantageously stores at least a one-month supply of the drug (e.g., a six-month supply) to reduce the number of refills required.

In certain embodiments, the refillable reservoir 100 comprises a multi-layered structure comprising a first wall 10 and a second wall 50 which is generally unpuncturable by the needle. For example, the first wall 10 of certain embodiments comprises a pliable, drug-impermeable polymer (e.g., silicone) layer that does not leak after being pierced by a needle, and the second wall 50 comprises a layer comprising less pliable, more mechanically robust material (e.g., a stiffer material such as a polymer or composite) or comprising a greater thickness of the same material used to fabricate the first wall 10. In certain embodiments in which the device 5 is implanted in or on the eye, the second wall 50 is placed adjacent to the sclera of the eye, and the greater mechanical strength of the second wall 50 advantageously limits the stroke of the needle used to puncture the first wall 10 to refill the reservoir 100, thereby protecting the eye from accidental punctures. In certain embodiments, the reservoir 100 is formed by bonding the first wall 10 and the second wall 50 either to each other or to one or more intervening layers, as described more fully below. In certain embodiments, the reservoir 100 includes integral mechanical support structures 60 which reduce the possible contact area between the first wall 10 and the second wall 50 and which prevent the reservoir 100 from collapsing completely. For example, the mechanical support structures 60 can comprise one or more protrusions (e.g., posts) extending from at least one of the first wall 10 and the second wall 50. Other mechanical support structures are also compatible with various embodiments described herein.

In certain embodiments, the cannula 110 comprises an elongate first portion 70 and a wall 30 defining a lumen 72 through the cannula 110. In certain embodiments, the cannula 110 includes one or more integral mechanical, support structures 74 in the lumen 72 of the cannula 110 to prevent fee cannula 110 from collapsing and occluding the lumen 72. For example, the mechanical support structures 74 can comprise one or more protrusions (e.g. posts) extending from an inner surface of the first portion 70 of the cannula 110 towards the wall 30 of the cannula 110. Mechanical support structures 74 of certain embodiments have a height which extends from the inner surface of the first portion 70 to the wall 30 and a width which extends less than the full width of the lumen 72. Other mechanical support structures are also compatible with various embodiments described herein.

In certain embodiments, the cannula 110 comprises an end 117 which is configured to be inserted into the patient and which comprises the outlet 115. In certain embodiments, the end 117 of the cannula 110 is tapered, to facilitate insertion into the eye. In certain other embodiments, the end 117 has rounded corners which advantageously allow easier insertion into the eye. The outer diameter of the cannula 110 of certain embodiments is less than or equal to the outer diameter of a 25-gauge needle. The outer diameter of the cannula 110 of certain other embodiments is less than 1 millimeter (e.g., 0.5 millimeter). In certain embodiments in which the device 5 is implantable in or on the eye, the outer diameter of the cannula 110 is sufficiently small to obviate the need for sutures at the insertion site and thereby to help maintain the integrity of the eye.

In certain embodiments, the cannula 110 comprises one or more flow regulator structures (e.g., valves) which advantageously maintain a constant flow rate such that the administered dosage depends on the duration that fluid flows through the cannula 110, rather than on the magnitude of an applied pressure which drives fluid flow through the cannula 110. Certain such embodiments advantageously provide more accurate control of the administered dosage. In certain embodiments, instead of, or in addition to, the one or more now regulator structures of the cannula 110, the reservoir 100 includes one or more such flow regulator structures.

In certain embodiments, the cannula 110 includes one or more fluid flow isolation structures (e.g., valves) which advantageously isolate the reservoir 100 from the body (e.g., the eye) during various operations involving the reservoir 100 (e.g., purging, cleaning, refilling). Certain such embodiments advantageously prevent exchange of fluid (in either direction) between the reservoir 100 and the patient's body. In certain embodiments, instead of, or in addition to the one or more fluid flow isolation structures of the cannula 110, the reservoir 100 includes one or more such fluid flow isolation structures.

In certain embodiments, the valve 120 is positioned at or near the end 117 of the cannula 110 which is insertable into the patient and comprises the outlet 115. The valve 120 in certain embodiments advantageously prevents unwanted diffusion of the drug from the device 5 into the patient's body (e.g., the eye). In certain embodiments, the valve 120 at or near the end 117 of the cannula 110 advantageously prevents backflow of material from, the patient's body into the cannula 110.

Figure 5:
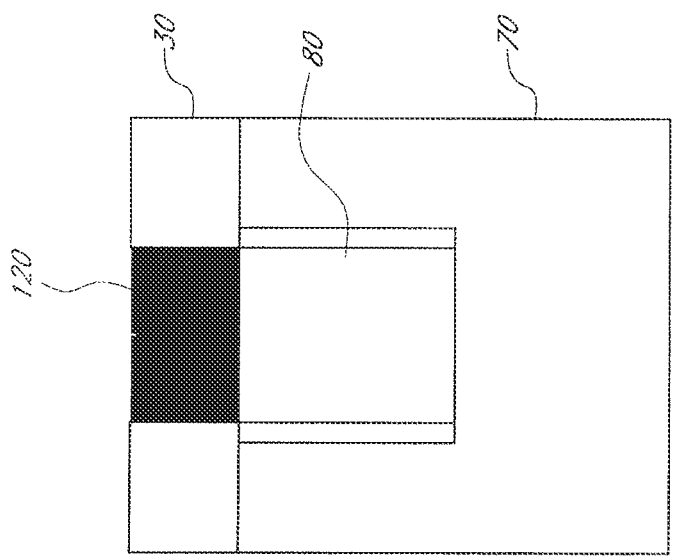
FIG. 5 shows a cross-sectional view of the device depicted in FIG. 2.

FIG. 5 schematically illustrates a cross-sectional view of an example valve 120 in accordance with certain embodiments described herein. The cross-sectional view of FIG. 5 is in the plane indicated by the dashed line of FIG. 2. FIG. 6A and FIG. 6B schematically illustrate cross-sectional views of an example valve 120 in the first and second positions in accordance with certain embodiments described herein. The valve 120 comprises a valve seat 80 and a movable element 122 having an orifice 40 therethrough. The movable element 122 of certain embodiments comprises a flexible portion of a wall 30 of the cannula 110. The portion of the wall 30 is movable between a first position (as schematically illustrated by FIG. 6B) in which the portion of the wall 30 does not contact the valve seat 80, and a second position (as schematically illustrated by FIG. 6A) in which the portion of the wall contacts the valve seat 80 such that the orifice 40 is occluded. Liquid can flow through the orifice 40 when the portion of the wall 30 is in the first position, but does not flow through the orifice 40 when the portion of the wall 30 is in the second position.

The valve seat 80 of certain embodiments comprises a protrusion (e.g., post) extending from an inner surface of the cannula 110 towards the movable element 122 (e.g., the flexible portion of the wall 30), as shown schematically by FIGS. 5, 6A, and 6B. In certain embodiments, the protrusion is substantially identical to the one or more integral mechanical support structures in the cannula 110 described above.

In certain embodiments, the portion of the wall 30 moves from the second position to the first position in response to pressure applied to the portion of the wall 30 by fluid within the cannula 110, as schematically illustrated by FIG. 6A and FIG. 6B. For example, manual pressure applied to one or more walls of the reservoir 100 can force fluid through the cannula 110 such that the fluid pressure opens the valve 120. In certain embodiments, the valve 120 opens only when the fluid pressure in the cannula 110 exceeds a predetermined threshold value greater than the fluid pressure outside the cannula 110. The valve 120 of certain embodiments advantageously remains closed when the fluid pressure in the cannula 110 is equal to or less than the fluid pressure outside the cannula 110 to prevent biological fluids from flowing backwards into the device 5.

Figure 7:
FIG. 7 is a photomicrograph of one embodiment of as assembled valve compatible with certain embodiments described herein.
Figure 8:
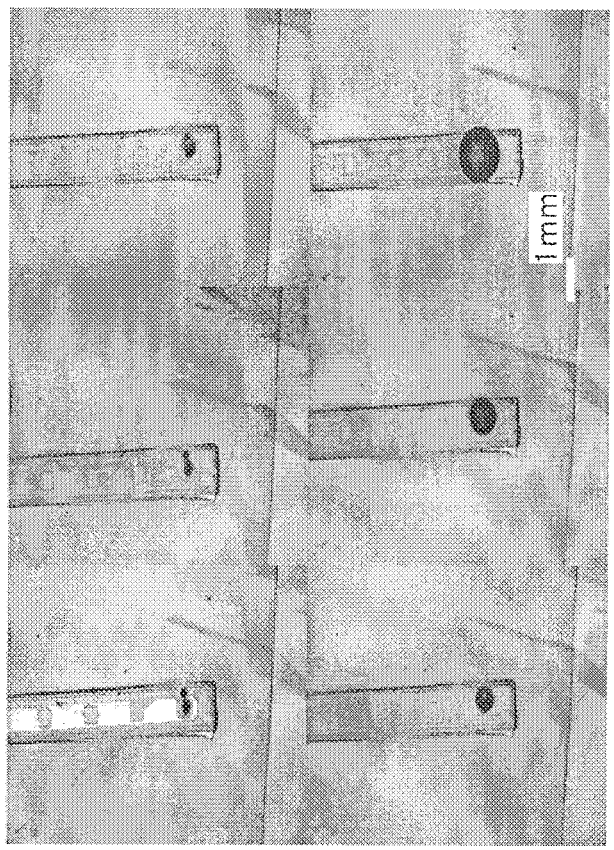
FIG. 8 is a series of photomicrographs illustrating the operation of an example valve in accordance with certain embodiments described herein.
Figure 9:
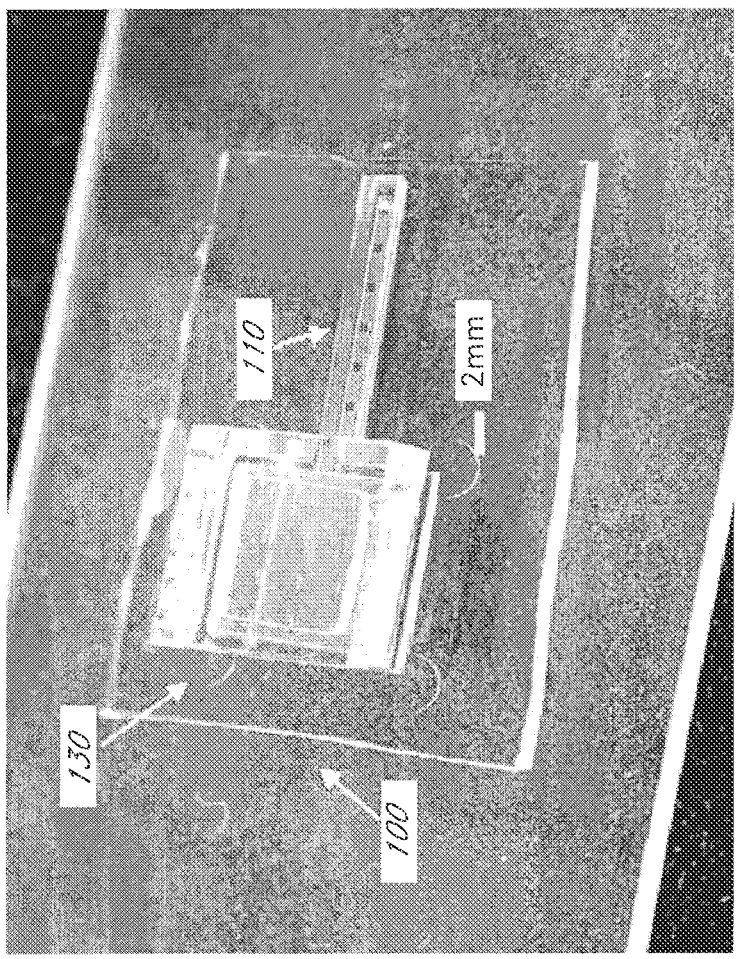
FIG. 9 shows an example of an assembled intraocular drug delivery device compatible with certain embodiments described herein.

FIG. 7 shows a photomicrograph of an example embodiment of the valve 120 of an assembled device 5 located at or near the end 117 of the cannula 110, FIG. 8 is a series of micrographs showing the delivery of a dye liquid from a device 5 compatible with certain embodiments described herein. FIG. 9 is a micrograph showing a device 5 having one or more suture tabs for affixing the device 5 to the implantation site (e.g., the eye).

Figure 10:
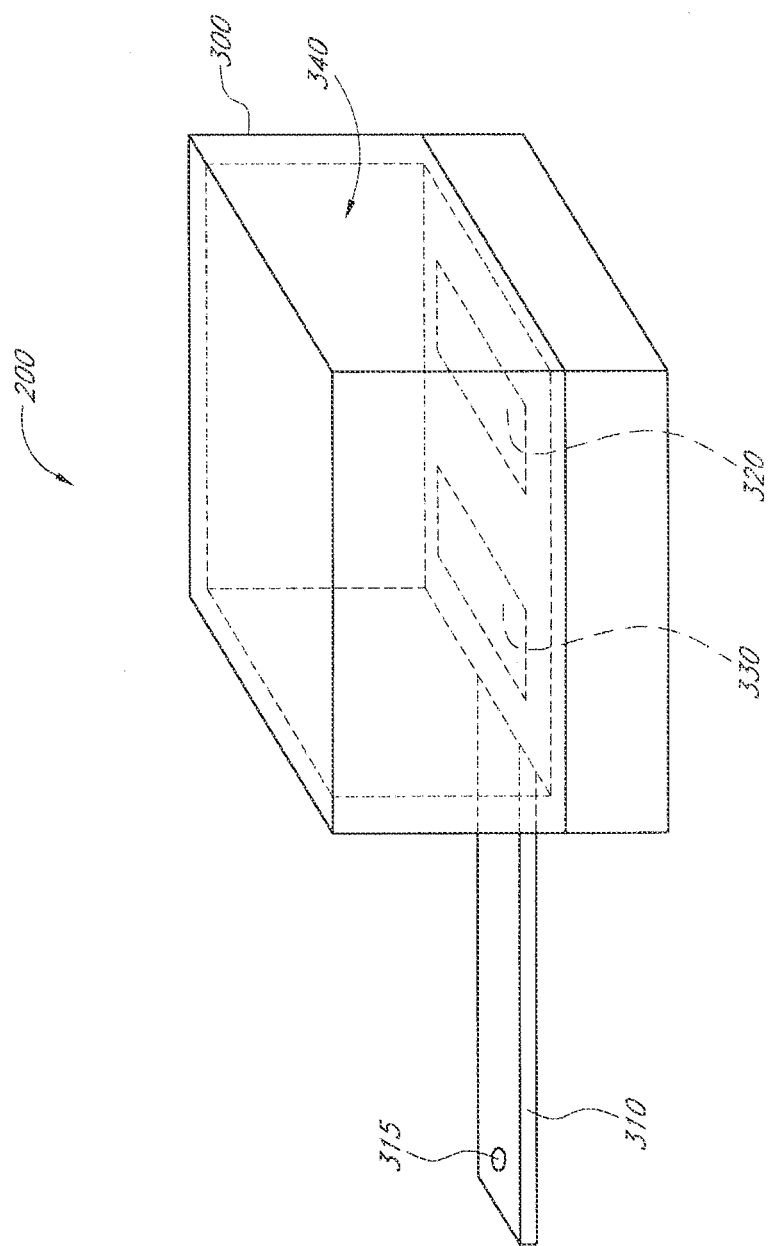
FIG. 10 schematically illustrates an example device utilizing electrolytic pumping in accordance with certain embodiments described herein.

FIG. 10 schematically illustrates another example device 200 in accordance with certain embodiments described herein. The device 200 comprises a reservoir 300 configured to contain a liquid comprising a therapeutic agent. The device 200 further comprises a cannula 310 in fluid communication with the reservoir 300. The cannula 310 has an outlet 315 configured to be in fluid communication with the patient. The device 200 further comprises a first electrode 320 and a second electrode 330. At least one of the first electrode 320 and the second electrode 330 is planar. The device 200 further comprises a material 340 in electrical communication with the first and second electrodes 320, 330. A voltage applied between the first electrode 320 and the second electrode 330 produces gas from the material 340. The gas forces the liquid to flow from the reservoir 300 to the outlet 315. In certain embodiments, the first and second electrodes 320, 330 serve as an electrolytic pump to drive liquid from the reservoir 300 through the cannula 315 to the outlet 315.

Electrolytic pumps use electrochemically-generated gases to generate pressure that dispense fluid (e.g., drug-containing liquid) from one location to another. For example, application of a suitable voltage across two electrodes (typically gold, palladium, or platinum) immersed in an aqueous electrolyte produces oxygen and hydrogen gases that can be used to apply pressure to a piston, membrane, or other transducer. Electrolysis of water occurs rapidly and reversibly in the presence of a catalyst such as platinum, which in the absence of an applied voltage catalyzes recombination of the hydrogen and oxygen to reform water. In certain embodiments described herein, the device uses electrolytically-generated gas to pump the drug from the reservoir through the cannula to the patient. In certain such embodiments, use of electrolytic pumping advantageously facilitates electronic control over drag delivery.

Electrolytic pumps offer several advantages for drug delivery. Their low-temperature, low-voltage and low-power operation suits them well for long-term operation in vivo. For ocular applications, electrolytic pumps advantageously produce negligible heat, and can also achieve high stress-strain relationships. Moreover, they lend themselves readily to use of microelectronics to control the voltage applied to the pump (and therefore the temporal pattern of pressure generation), which allows device operation in either bolus and/or continuous dosage mode. Radiofrequency transmission/reception may also be used to provide wireless power and control of the microelectronic circuitry to operate the pump.

Electrolysis in a chamber in fluid communication with its exterior generates gases that force working fluid out of the chamber. Reversing the polarity of the applied voltage can reverse the process, thereby restoring the chamber to its original state. Since a small trickle charge can prevent this reverse process, this device can be held in place with little power (i.e., the device is latchable).

Figure 11:
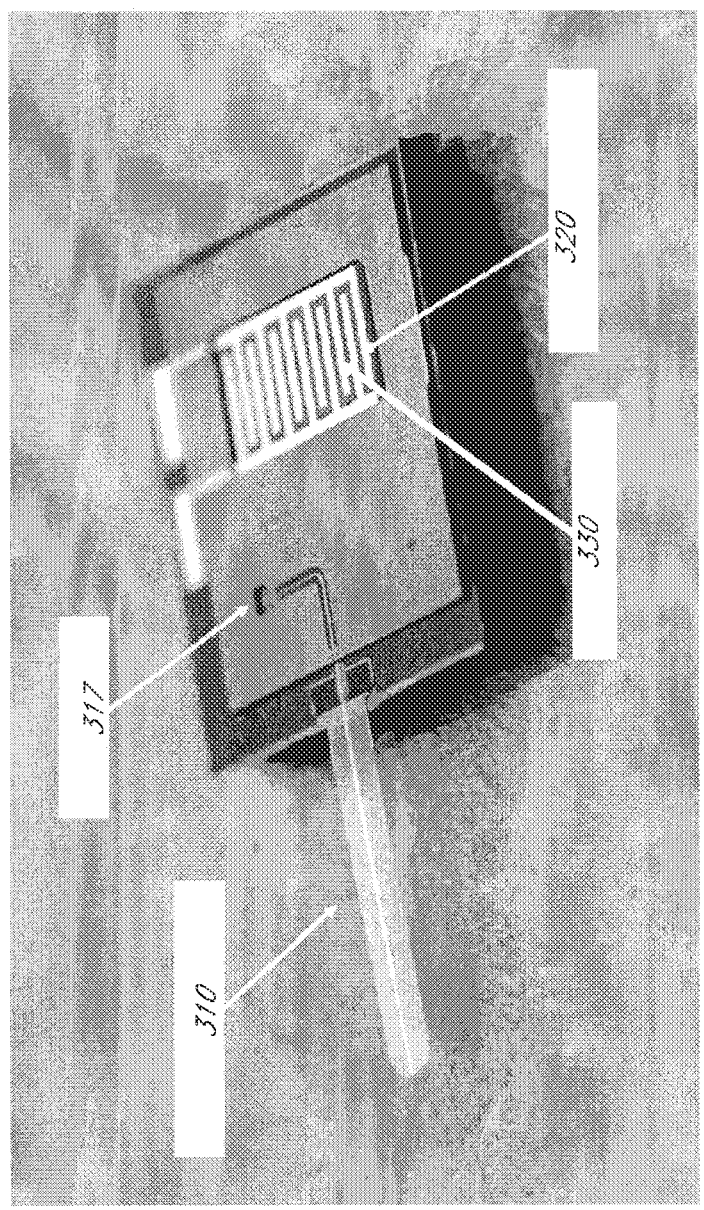
FIG. 11 shows the base layer of an example device showing integrated drug delivery cannula and electrolysis electrodes.

FIG. 11 is a view of a first portion 350 of an example device 200 in accordance with certain embodiments described herein. The first portion 350 includes the cannula 310, the first electrode 320, and the second electrode 330 of an example device 200 in accordance with certain embodiments described herein. For the device 200 of FIG. 11, the material 340 also comprises the drug to be administered to the patient. In certain embodiments, the cannula 310 comprises parylene and is in fluid communication with the reservoir 300 through a pump outlet 317. The first electrode 320 and the second electrode 330 of FIG. 11 are interdigitated with one another. Such a configuration can advantageously ensure that the material 340 is in electrical communication with both the first electrode 320 and the second electrode 330.

Figure 12B:
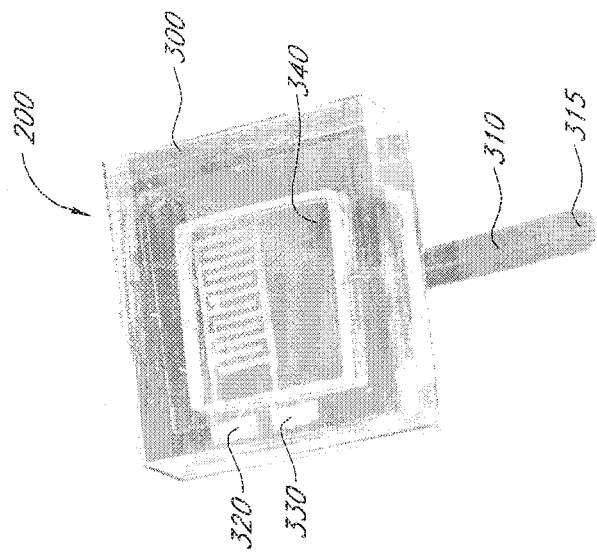
FIGS. 12A and 12B show an example of the base layer next to a reservoir cap and with an assembled reservoir, respectively, in accordance with certain embodiments described herein.
Figure 12A:
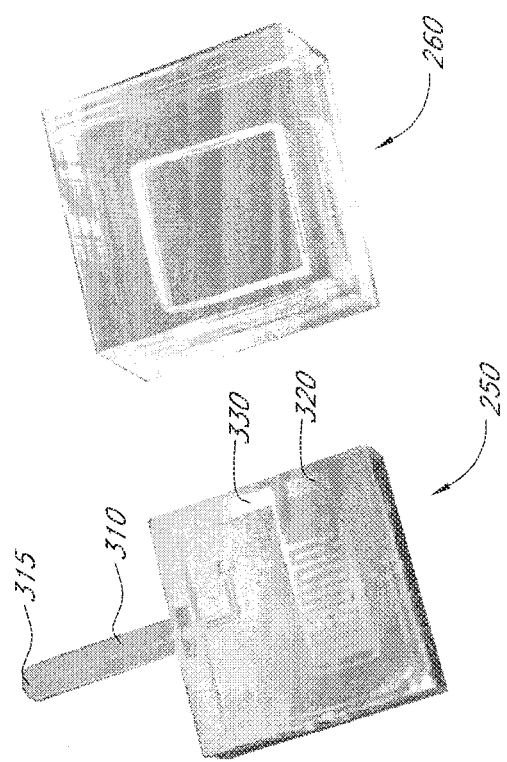

FIGS. 12A and 12B are photographs of the first portion 250 of the device 200 and a second portion 260 of the device 200. The second portion 260 is mountable onto the first portion 250, thereby forming a reservoir 300 therebetween, with the first electrode 320 and the second electrode 330 inside the reservoir 300. The second portion 260 of certain embodiments comprises a liquid- and gas-impermeable material (e.g., silicone) which is self-sealing to repeated punctures, as described above.

FIGS. 13A and 13B schematically illustrate a top- and a side-cross-sectional view, respectively, of a first portion 250 of another example device 200 which utilizes electrolytic pumping in accordance with certain embodiments described herein. The first portion 250 comprises a support layer 305, a first electrode 320, and a second electrode 330. The first and second electrodes 320, 330 are over the support layer 305, and at least one of the first electrode 320 and the second electrode 330 is planar.

The support layer 305 of certain embodiments is liquid- and gas-impermeable, and in certain such embodiments, is also electrically insulative such that, absent any conductive material above the support layer 305, the first electrode 320 and the second electrode 330 are electrically insulated from one another. The first electrode 320 and the second electrode 330 are configured to be in electrical communication with a voltage source (not shown) which applies a voltage difference across the first electrode 320 and the second electrode 330.

As schematically illustrated in FIGS. 13A and 13B, in certain embodiments, both the first and second electrodes 320, 330 are planar and are co-planar with one another. In certain embodiments, at least one of the first electrode 320 and the second electrode 330 is patterned to have elongations or fingers within the plane defined by the electrode. For example, as schematically illustrated by FIG. 13A, the first electrode 320 is elongate and extends along a generally circular perimeter with radial elongations 322 which extend towards the center of the generally circular perimeter of the first electrode 320. The second electrode 330 of certain embodiments has a center elongate portion 332 with generally perpendicular elongations 334 extending therefrom. In certain embodiments, the elongations 334 define a generally circular perimeter within the generally circular perimeter of the first electrode 320, as schematically illustrated by FIG. 13A. Other shapes and configurations of the first electrode 320 and the second electrode 330 are also compatible with certain embodiments described herein.

The first portion 250 of certain embodiments further comprises an outer wall 360 which is liquid- and gas-impermeable. As described more fully below, the outer wall 360 is configured to be bonded to a corresponding wall of the second portion 260 of the device 200.

The first portion 250 of certain embodiments further comprises a first structure 370 between the first electrode 320 and the second electrode 330. As schematically illustrated in FIG. 13A, in certain embodiments, the first structure 370 comprises a generally circular wall extending generally perpendicularly from the support layer 305. The first structure 370 of certain embodiments has one or more fluid passageways 372 through which a liquid can flow between a first region 380 above the first electrode 320 and a second region 385 above the second electrode 330, as described more fully below. In certain embodiments, the first structure 370 comprises a liquid-permeable but gas-impermeable barrier between the first and second regions 380, 385.

In certain embodiments, the first portion 250 further comprises a second structure 374 above the first electrode 320 and a third structure 376 above the second electrode 330. In certain embodiments, the second structure 374 is mechanically coupled to the first structure 370 and the outer wall 360, as schematically illustrated by FIG. 13B, such that the support layer 305, the outer wall 360, the first structure 370, and the second structure 374 define a first region 380 containing the first electrode 320. In certain embodiments, the third structure 376 is mechanically coupled to the first structure 370, as schematically illustrated by FIG. 13B, such that the support layer 305, the first structure 370, and the third structure 376 define a second region 385 containing the second electrode 330.

In certain embodiments, at least one of the second structure 374 and the third structure 376 is flexible and is liquid- and gas-impermeable. For example, at least one of the second structure 374 and the third structure 376 comprise a flexible membrane (e.g., corrugated parylene film). At least one of the second structure 374 and the third structure 376 is configured to expand and contract with increases and decreases in pressure in the corresponding first region 380 and/or second region 385. In certain such embodiments, both the second structure 372 and the third structure 374 comprise portions of the same flexible membrane, as schematically illustrated by FIG. 13B.

In certain embodiments, a pair of interdigitated electrodes is fabricated on the same substrate as a parylene cannula for directing drugs. The electrolysis reaction can either occur in the same chamber containing the drug to be delivered or in a separate electrolysis chamber adjacent to the drug reservoir. In the latter case, the working fluid, or electrolyte, is sealed inside the electrolysis chamber.

FIGS. 14A and 14B schematically illustrate a top view and a side-cross-sectional view of an example device 200 comprising the first portion 350 and a second portion 260 in accordance with certain embodiments described herein. The second portion 260 of certain embodiments comprises a liquid-impermeable wall which is configured to be bonded to corresponding portions of the first portion 250 of the device 200. As schematically illustrated by FIGS. 14A and 14B, the second portion 260 of certain embodiments is bonded to the outer wall 360 of the first portion 250 such that the second portion 260, the second structure 374, and the third, structure 376 define a reservoir 390 configured to contain a drug.

The device 200 of certain embodiments further comprises a cannula 110 with one or more outlets 115. The cannula 110 is configured to be positioned such that the one or more outlets 115 are in fluid communication with the patient's body (e.g., the eye). In certain embodiments, the cannula 110 comprises parylene and has a generally elongate shape with a lumen therethrough in fluid, communication with the reservoir 390 and the one or more outlets 115, as schematically illustrated by FIG. 14B.

In certain embodiments, the first region 380 and the second, region 385 contain a material 390 which emits gas when a sufficient voltage is applied to the material 390. For example, in certain embodiments, the material 390 comprises water which is electrolytically separated by an applied voltage into hydrogen gas and oxygen gas. As schematically illustrated by FIG. 14B, in certain embodiments, both the second structure 374 and the third structure 376 comprise liquid- and gas-impermeable flexible membranes, and gas generated at the first electrode 320 increases the pressure in the first region 380, thereby flexing the second structure 374 towards the reservoir 390. Furthermore, gas generated at the second electrode 330 increases the pressure in the second region 385, thereby flexing the third structure 376 towards the reservoir 390. The flexing of at least one of the second structure 374 and the third structure 376 forces liquid (e.g., containing a therapeutic agent) to flow from the reservoir 390, through the cannula 110, to the one or more outlets 115.

In certain embodiments, the device 200 advantageously restricts gas produced at the first electrode 320 from mixing with gas produced at the second electrode 330. For example, as schematically illustrated by FIG. 14B, when the material 390 comprises water, hydrogen gas produced at one electrode (e.g., the first electrode 320) is generally restricted to the first region 380 and gas produces at the other electrode (e.g. the second electrode 330) is generally restricted to the second region 385. Gas generated at either or both of first and second electrodes 320 and 330 increases the volume of either or both of first chamber 300 or second chamber 330, expanding electrolytic chamber membrane 360 and thereby forcing liquid to flow from reservoir 300 through cannula 110.

Figure 15A:
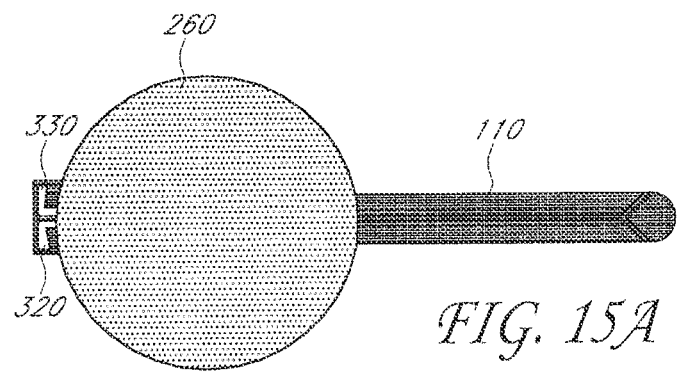
FIGS. 15A-15D show successive cut-away views of a drug reservoir and pump chamber compatible with certain embodiments described herein.
Figure 15B:
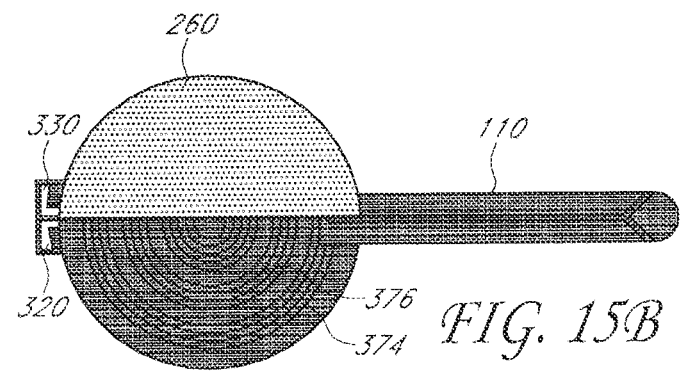
Figure 15C:
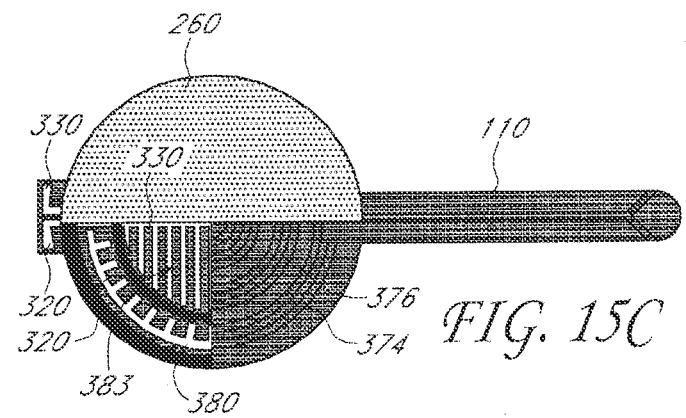
Figure 15D:
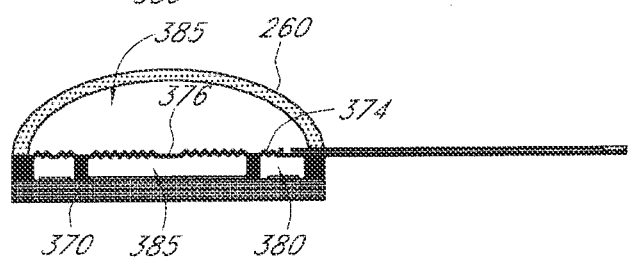

FIGS. 15A-15D schematically illustrate various views of the example device 200 of FIGS. 14A and 14B. FIG. 15A schematically illustrates a top view of the device 200 with the first electrode 320, the second electrode 330, the second portion 260, and the cannula 110. FIG. 15B schematically illustrates a top-partially cut-away view that shows the first electrode 320, the second electrode 330, the second portion 260, the cannula 110, and the second structure 374 and the third structure 376. As shown in FIG. 15B, the second structure 374 and the third structure 376 are portions of a membrane extending across the first portion 250 of the device 200. FIG. 15C schematically illustrates a further top-partially cut-away view that shows a portion of the first region 380, the first electrode 320 in the first region 380, the second region 385, the second electrode 330 within the second region 385, the first structure 370, and the outer wall 360, as well as the second portion 260 and the cannula 110. FIG. 15D schematically illustrates a side cross-sectional view of the device 200 which does not contain either the material 390 or the drug, and which corresponds to the filled device 200 schematically illustrated by FIG. 14B.

FIG. 16 schematically illustrates various views of an example device 200 comprising an injection port 410 configured to receive an injection needle 420. The injection port 410 of certain embodiments is part of the first portion 250 of the device 200, while in certain other embodiments, the injection port 410 is part of the second portion 260 of the device 250. The injection port 410 is in fluid communication with the reservoir of the device 200 to facilitate refilling of the device 200 while the device 200 is implanted, in addition, the device 200 schematically illustrated by FIG. 16 includes suture tabs 400 for fastening the device 200 to the patient's body (e.g., the surface of the eye).

Figure 17:
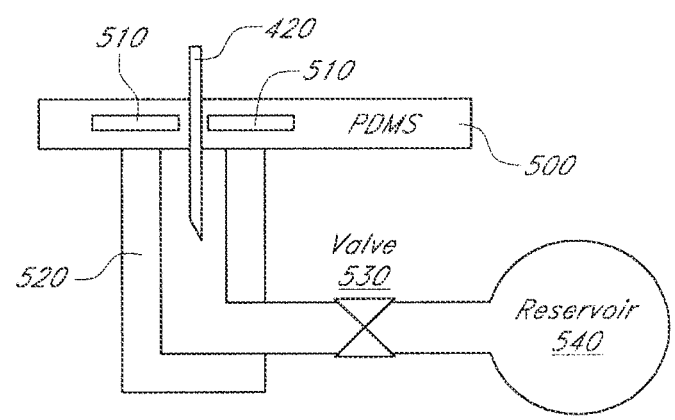
FIG. 17 shows the internal structure of one type of injection port on the reservoir compatible with certain embodiments described herein.

FIG. 17 schematically illustrates the internal structure of an example injection port 410 compatible with certain embodiments described herein. Injection needle 420 pierces injection port surface 500 through needle injection guide 510, and thereby gains access to injection vestibule 520. Injection of fluid, into the vestibule 520 forces liquid through the injection port valve 530 and into the reservoir 540.

In certain embodiments, the device 200 is powered by an internal battery (not shown), while in certain other embodiments, the device 200 is powered by an external source (not shown). In certain embodiments, both a battery and an external source are used. For example, even though the power can be recharged wirelessly, a smaller battery may be used to store the power for a week, thereby advantageously keeping the device small and minimally invasive.

The external source can be electrically coupled to the device 200 using wires or by wireless means (e.g., radiofrequency transmitter/receiver). By utilizing an external source and avoiding the use of an internal battery, the device 200 can advantageously be made smaller, and therefore less invasive. In addition, by wirelessly controlling the operation of the device 200 (e.g., turning it on and off), a handheld transmitter can be programmed to send a signal that communicates with the device to power the device when needed. For example, at times when less drug is needed, less power is transmitted, and less drug is pumped. There will, be some threshold cutoff on the external power applicator for example that limits the implant from pumping too much drug. Wireless power is through the use of coils built into the implant and the external transmitter through a process of inductive powering.

In certain embodiments, the device 200 includes an integrated circuit for controlling operation of the device 200.

Examples of integrated circuits compatible with certain such embodiments include but are not limited to, single-chip application-specific integrated circuits (ASICs) and application-specific standard products (ASSPs) that have become more common for implantable medical applications. Certain such integrated circuits advantageously consume as little power as possible, e.g., to extend battery life, and therefore lengthen the time between invasive replacement procedures. The ASIC will be the predominant chip for this implant that will help add additional features in its current low power embodiment. In certain embodiments, the device can include microelectronics to control the dosage and release, sensors for feedback control, anchoring structures to hold, the device in place, supports to keep the reservoir from collapsing on itself when emptied, filtering structures, additional valves for more accurate flow control, a flow regulator to remove the adverse effects of pressure on drug delivery, and a programmable telemetry interface.

In certain embodiments, the device comprises a plurality of structural layers which are bonded together to form a reservoir configured to contain a liquid and a cannula in fluid communication with the reservoir. The cannula has an outlet configured to be in fluid communication with the patient. For example, the device can comprise three individual layers of a biocompatible polymer, such as polydimethylsiloxane, that are fabricated separately and then bonded together, as schematically illustrated by FIGS. 1 and 2. In this example structure, the lower layer forms the base of the device outlining the reservoir, the cannula, and the valve. This lower layer contains posts that mechanically support the cannula and the reservoir to prevent it from collapsing and that provide the valve seat for the valve, as described more fully above. The middle layer forms the cannula and the movable portion of the valve. The upper layer forms the upper half of the reservoir.

Figure 18A:
FIGS. 18A-18K show an example process flow for fabricating a silicon mask and making a molded polydimethylsiloxane (PDMS) layer with silicon shown with dark shading, parylene shown with no shading, and PDMS shown with diagonal line shading.
Figure 18G:
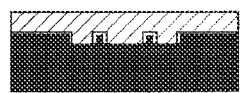
Figure 18B:
Figure 18H:
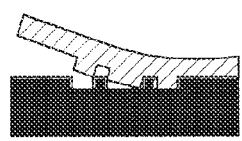
Figure 18C:
Figure 18I:
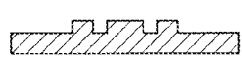

In certain such embodiments, at least one of the structural layers is formed rising a lithographic process (e.g., soft lithography). FIGS. 18A-18K schematically illustrates an example lithographic process in accordance with certain embodiments described herein. As schematically illustrated by FIG. 18A, a substrate (e.g., silicon wafer) is provided. As schematically illustrated by FIG. 18B, a photoresist layer is formed on the substrate (e.g., by spin-coating a light-sensitive liquid onto the substrate). Suitable photoresists are well-known to those skilled in the art, and include, but are not limited to, diazonaphthoquinone, phenol formaldehyde resin, and various epoxy-based polymers, such as the polymer known as SU-8. As schematically illustrated by FIG. 18C, the photoresist layer is patterned to cover a first portion of the substrate and to not cover a second portion of the substrate. For example, ultraviolet light can be shone through a mask onto the photoresist-coated wafer, thereby transferring the mask pattern to the photoresist layer. Treatment of the water by well-known photoresist development techniques can be used to remove the portions of the photoresist layer that were exposed to the ultraviolet light. Persons skilled in the art of lithographic techniques are able to select appropriate materials and process steps for forming the patterned photoresist layer in accordance with certain embodiments described herein.

Figure 18D:
Figure 18J:
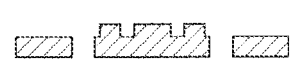
Figure 18E:
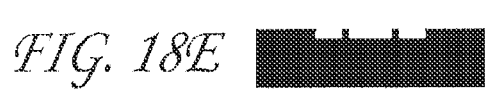
Figure 18K:
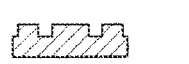
Figure 18F:
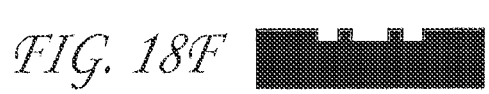

As schematically illustrated by FIG. 18D, the portion of the substrate that is not covered by the patterned photoresist layer is etched (e.g., by deep reactive-ion etching), thereby leaving untouched the portions of the silicon wafer protected by the photoresist layer. As schematically illustrated by FIG. 18E, the patterned photoresist layer is removed. For example, after washing with a solvent, such as acetone, the photoresist layer is removed and the entire wafer can be cleaned through use of oxygen plasma to remove any remaining photoresist. As schematically illustrated by FIG. 18F, a mold release layer (e.g., parylene, a widely-used polymer of p-xylene) is formed on the substrate to facilitate removal of the PDMS layer from the silicon wafer. Other materials can be used as the mold release layer in other embodiments. As schematically illustrated by FIG. 18G, the structural layer (e.g., PDMS silicone) is formed on the mold release layer. For example, PDMS can be poured over the silicon wafer and allowed to cure either by standing at room temperature or accelerated, by heating (e.g., to 75° C. for 45 minutes). As schematically illustrated by FIG. 18H, the structural layer is removed from the substrate, thereby providing the structural layer schematically illustrated by FIG. 18I. In certain embodiments, the molded PDMS layer contains multiple copies of the structural layer, and each copy of the structural layer is separated from the others. Excess material can be removed from the structural layer, as schematically illustrated by FIG. 18J, thereby providing the structural layer schematically illustrated by FIG. 18K, ready for assembly with the other structural layers.

The individual structural layers can be assembled and bonded together in certain embodiments by treating the surface of one or more of the structural layers with oxygen plasma for about one minute, although the time is not critical. Oxygen plasma changes the surface of the polydimethylsiloxane from hydrophobic to hydrophilic.

In certain embodiments, the bottom layer and the middle layer are placed into a plasma chamber with the sides that are to be bonded facing the plasma. Once the surfaces have been treated, the two pieces can be aligned with the aid of any polar liquid (e.g., ethanol, water). The liquid preserves the reactive hydrophilic surface providing more time to align the two layers. It also makes the pieces easier to manipulate for alignment since it lubricates the surfaces, which are otherwise sticky. The two-layer assembly can then be placed back into the chamber along with the top layer and the treatment and alignment procedure repeated. The entire assembly can then be baked (at 100° C. for 45 minutes) to reinforce the bonds. The bonded silicone appeared homogeneous by SEM and optical observation. Tests with pressurized $N_2$ showed that the bonded silicone assembly withstood pressures of at least 25 psi.

In certain embodiments, the orifice 40 is made by, for example, inserting a small diameter coring needle into a sheet of silicone rubber that later forms the upper surface of the cannula. Other methods can also be used to generate this feature. The coring needle removes material to create the orifice. The valve seat 80 of certain embodiments is a post that protrudes from the bottom of the cannula 110 and extends the height of the channel to meet the top of the cannula. During assembly, the orifice 40 is centered over the valve seat 80 and rests on it to form the valve. In this configuration, the valve is said to be "normally-closed" and fluid will not pass through. Fluid, pressure in the cannula 110 exceeding a certain value (cracking pressure) opens the valve and allows fluid to exit the device through a gap between valve seat 80 and movable element 122, as schematically illustrated by FIGS. 6A and 6B.

FIGS. 19A-19M schematically illustrate an example process for forming a device that includes electrolytic pumping. While FIGS. 19A-19M schematically illustrate example processes for forming a device utilizing electrolytic pumping, other methods can be used in accordance with certain embodiments described herein.

Figures 19A, 19B, 19C, 19D, 19E, 19F, 19G, 19H, 19I, 19J, 19K, 19L, 19M:
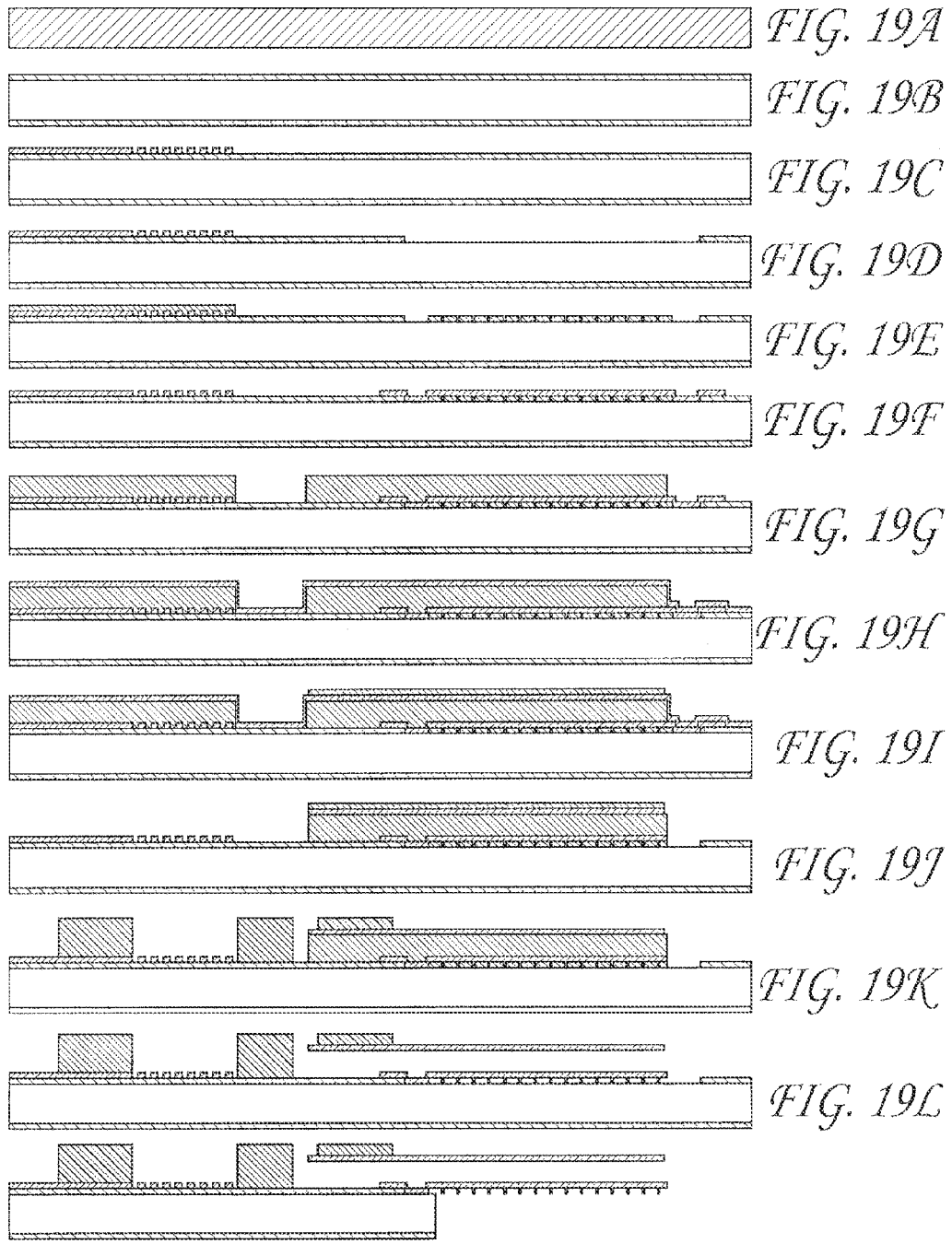
FIGS. 19A-19M show an example process flow to fabricate the base layer of an implantable drug delivery device that includes electrodes for electrolytic pumping and an integral cannula in accordance with certain embodiments described herein.

As schematically illustrated by FIG. 19A, a bare silicon substrate is provided and as schematically illustrated by FIG. 19B, a dielectric layer (e.g., a thermal silicon dioxide layer about 4000 Å thick) is grown on the silicon substrate. This silicon oxide layer electrically insulates the substrate and electrolysis electrodes.

Electrolysis electrodes (e.g., made of Ti/Pt, 200 Å/2000 Å thick, respectively) are formed over the dielectric layer (e.g., deposited and lithographically patterned), as schematically illustrated by FIG. 19C. The dielectric layer is patterned and etched briefly with $XeF_2$ to remove a portion of the dielectric layer, thereby exposing a portion of the substrate. This process can also roughen the exposed silicon surface, as schematically illustrated by FIG. 19D. A first sacrificial photoresist layer (e.g., 5 μm thick) can be span and patterned on the substrate, as schematically illustrated by FIG. 19E. The first sacrificial photoresist layer facilitates the release of the cannula from the supporting silicon substrate at the end of the fabrication process. A first structural layer (e.g., 7.5 μm thick parylene layer) can be deposited and patterned on the first sacrificial layer, as schematically illustrated by FIG. 19F, which will become the bottom wall of the drag delivery cannula. As schematically illustrated by FIG. 19G, a second sacrificial layer (e.g., 25 μm thick photoresist layer, spun and patterned) can be formed over the first structural layer. As schematically illustrated by FIG. 19H, a second structural layer (e.g., 7.5 μm thick parylene) can be deposited on the second sacrificial layer, and which will become the top and side walls of the cannula. The first and second structural layers can then be patterned, as schematically illustrated by FIGS. 19I and 19J. For example, a Cr/Au etch mask layer for removing unwanted parylene (200 Å/2000 Å thick, respectively) can be deposited and patterned on the substrate, as schematically illustrated by FIG. 19I. The parylene can be patterned in an oxygen plasma through use of the Cr/Au masking layer, as schematically illustrated by FIG. 19J. A third structural layer (e.g., an SU-8 photoresist layer 70 μm thick) can be spun and patterned on the substrate, as schematically illustrated by FIG. 19K. The SU-8 layer supports the cannula and prevents its collapse when a drag reservoir is attached to the base layer. The sacrificial photoresist layers are then removed by dissolving them in acetone, as schematically illustrated by FIG. 19L. The cannula can be peeled up from the surface of the roughened silicon substrate and broken off the silicon substrate directly beneath the cannula to form a free-standing cannula, as schematically illustrated by FIG. 19M.

In certain embodiments, the device is implanted by attaching the main body of the device to the top of the eye and inserting the cannula into the anterior or the posterior segment of the eye. The device is affixed to the eye through use of current ophthalmic techniques such as sutures or eye tacks, in certain embodiments, a method of using the device comprises applying a first voltage between the first electrode and the second electrode to produce gas from the material in electrical communication with the first and second electrodes. The gas forces liquid from the reservoir to flow from the reservoir to the outlet of the device. In certain embodiments, the method further comprises applying a second voltage between the first electrode and the second electrode to produce the material from the gas. In this way, the device is used in a reversible manner in which the material can be regenerated from the gases, thereby avoiding having to refill the device with the material. In certain embodiments the material comprises water and the gas comprises hydrogen gas and oxygen gas. In certain embodiments, the first voltage and the second voltage are opposite in sign.

Example

A device having a flexible parylene transscleral cannula allowing targeted delivery to tissues in both the anterior and posterior segments of the eye is described below. The electrochemically driven drug delivery device was demonstrated to provide flow rates suitable for ocular drug therapy (pL/min to μL/min). Both continuous and bolus drug delivery modes were performed to achieve accurate delivery of a target volume of 250 nL. An encapsulation packaging technique was developed for acute surgical studies and preliminary ex vivo drug delivery experiments in porcine eyes were performed.

Pharmaceuticals for eye treatment advantageously penetrate the protective physiological barriers of the eye such as the cornea, sclera, and the blood-retina barrier and to target difficult-to-reach intraocular tissues such as the ciliary body, retina, and angle.

With miniaturized MEMS devices, precise delivery in either bolus or continuous mode is possible. The advantages of MEMS fabrication for producing miniaturized and efficient drug delivery systems are capable of targeted delivery to an interior tissues, refutable for long-term use, and automated to address patient compliance.

The electrolysis of water results in the phase transformation of liquid to gas and provides the actuation used to drive drug deliver in this example device. The net result of the electrolysis is the production of oxygen and hydrogen gas that contributes to a volume expansion of about a thousand times greater than that of the water used in the reaction. This gas evolution process proceeds even in a pressurized environment (e.g., 200 MPa). To drive gas generation and thus pumping, current control is useful for its direct correlation to pump rate and volume. If current is used to drive the reaction, the theoretical pump rate ($q_{theoretical}$ in m$^3$/s) at atmospheric pressure is given by: $q_{theoretical}=0.75$ $(I/F)V_m$, where I is current in amperes, F is Faraday's constant and $V_m$ is the molar gas volume at 25 degrees Celsius and atmospheric pressure. The theoretical generated or dosed gas volume ($V_{theoretical}$ in m$^3$) can be determined by: $V_{theoretical}=q_{theoretical}t$, where t is the duration (in sec) that the current is applied. The efficiency (η) of an electrolysis actuator as a pump can be defined, as: $\eta=V_{experimental}/V_{theoretical}$, where $V_{experimental}$ is the actual volume of the generated hydrogen and oxygen gases. Efficiency in electrochemical systems is affected by a number of parameters including electrode (material, surface area, geometry, and surface conditions), mass transfer (transport mode, surface concentration, adsorption), external (temperature, pressure, and time), solution (Bulk concentration of electroactive species, concentration of other species, solvent), and electrical (potential, current, quantity of electricity).

The electrolysis pump consists of two interdigitated platinum, electrodes immersed in an electrolyte. This electrode geometry improves pumping efficiency by reducing the current path through the solution which serves to lower the heat generation. The gasses generated result in an internal pressure increase in the sealed reservoir which causes drug to be delivered through the cannula and into the eye. Electrolysis is a reversible process and ceases when the applied signal is turned off, thereby allowing the gradual recombination of hydrogen and oxygen to water.

Using the device illustrated by FIGS. 11, 1A, and 12B, pumped drug entered a flexible transscleral cannula through a small, port connected to the pump while the generated gases remain trapped inside the reservoir. Parylene was selected as the cannula material for its mechanical strength, biocompatibility, and ease of integration. It is a USP Class VI material suitable for the construction of implants and is well-established as a MEMS material. The pump/cannula portion was fabricated using silicon micromachining and the reservoir portion by the casting of silicone rubber against a master mold.

The fabrication process of the pump and cannula chip started with a thermally oxidized silicon substrate (5000 Angstroms). LOR 3B (MIcroChem Corp., Newton, Mass.) was spun on at 3 krpm followed by AZ 1518 (AZ Electronic Materials, Branchburg, N.J.) at 3 krpm. Ti—Pt (200/2000 Angstroms was e-beam evaporated and patterned by lift-off in ST-22 photoresist stripper (ATMI, Banbury. CT) to define the interdigitated electrodes. A second lithography step was performed (AZ 1518 at 3 krpm) to define the cannula footprint. The oxide layer was etched using buffered HF acid to expose the Si below. The photoresist was stripped, then the exposed Si was roughened by two cycles of XeF2 etching. The first sacrificial photoresist layer (AZ 4620 spun at 2.75 krpm and hard baked to yield a 5 micron thick layer) was applied to facilitate release of the cannula from the substrate. The first parylene C layer (7.5 microns) forming the bottom of the cannula was deposited followed by thermal evaporation of 2000 angstroms thick Cr etch mask. Following lithography (AZ 4620 at 500 rpm) the CR is etched in CR-7 (Cyanteck, Fremont, Calif.) and the photoresist is tripped. The parylene layer is then patterned in an oxygen plasma and the Cr etch mask is removed using Cr-7. A second photoresist sacrificial layer was deposited (AZ 4620 span at 450 rpm and hard baked to yield a 25 micron thick layers to define the channel height. A second parylene layer of 7.5 microns was deposited to complete the cannula. To define the cannula from the parylene/photoresist/parylene sandwich, Ti/Au (200/2000 angstroms) was deposited as an etch mask. The etch mask was pattered (AZ 4620 spun at 425 rpm) and etched first with Au etchant TFA (Transene Company, Inc., Danvers, Mass.) and then 10% HF. Finally, the sandwich is etched in oxygen plasma and the masking layer is stripped (Au etching TFA and 10% HF). Following the etch, the entire wafer was cleaned in 5% HF dip and by exposure to oxygen plasma. SU-8 2200 (MicroChem Corp., Newton, Mass.) was spun at 2200 rpm resulting in a 70 micron thick layer after post baking. The sacrificial photoresist was removed by dissolving in a 40 degree Celsius acetone solution for one day. The individual cannulas were released manually by gently lifting them of the substrate. Finally, individual dies were separated and the remaining silicon beneath each cannula was removed by scribing and breaking it off.

The pump chip containing the electrolysis actuator and cannula was combined with the drug reservoir and electrical wiring. The final product after assembly is shown in FIGS. 12A and 12B. Electrical wires were bonded to the electrode contact pads using Ohmex-AG conductive epoxy (Transene Company, Inc., Danvers, Mass.). The epoxy was cured at 150 degrees Celsius for 15 hours under vacuum. The pump chip and reservoir were then assembled using an encapsulation technique based on silicone soft lithography as described above.

To shape the package to fit comfortably on the curved contour of the eyeball, a silicone spacer (Sylgard 184, Dow Corning, Midland, Mich.) was casted against a stainless steel sphere of 17.5 mm in diameter. This layer of partially cured, silicone (10:1 base to curing agent ratio, cured at 65 degrees Celsius for 20 minutes. The sphere was removed and the resulting crater was filled with wax. A silicone reservoir was prepared by casting against a conventionally machined acrylic mold, partially-cured at 65 degrees Celsius for 20 minutes. The mold produces a reservoir with internal dimensions of 6 mm×6 mm×1.5 mm. The silicone reservoir was aligned to the chip and spacer and the parylene cannula, was then immersed in DI water which serves a mask to prevent coating by silicone rubber during the encapsulation step, thereby exploiting the hydrophobicity of silicone rubber. The stack was immersed in silicone prepolymer and cured at room temperature for 24 hours. Extraneous silicone material was removed from the device to complete the assembly process.

To investigate the performance of the electrolysis pump, experiments examining continuous delivery, bolus delivery, pump efficiency, gas recombination, and backpressure were conducted. For these tests, a custom testing apparatus was laser-machined (Mini/Helix 8000, Epilog, Golden, Colo.) in acrylic. The experimental setup consisted of a computer-controlled CCD camera (PL-A662, pixeLINK, Ottawa, Canada) for collecting flow data from a calibrated micro-pipette (Accu-Fill 90, Becton, Dickinson and Company) attached to the output port of the test fixture. Testing was performed using deionized water as the electrolyte. The electrolysis was initiated under constant current conditions (50 µA to 1.25 mA) for continuous delivery operation. The relationship between efficiency and recombination of hydrogen and oxygen to water was studied.

Bolus delivery was also examined. A constant current pulse (0.5, 1.0, and 1.5 mA) was applied for 1, 2, and 3 seconds. Repeated trials were performed (n=4) to obtain average dosing volume. Normal intraocular pressure GOP) ranges from 5-22 mm Kg (15.5±2.6 mmHg (mean±SD)), Values outside this range correspond to abnormal intraocular pressure which is a characteristic of glaucoma (>22 mmHg). Thus, it is helpful to characterize pump performance under these physiologically relevant conditions. The experimental setup was modified to include a water column attached to the outlet of the micro-pipette. Backpressure was applied to the drug delivery device by adjusting the height of the water column. Data was collected for backpressures corresponding to normal IOP (20 mmHg) and abnormal IOP (0 and 70 mmHg).

Figure 20:
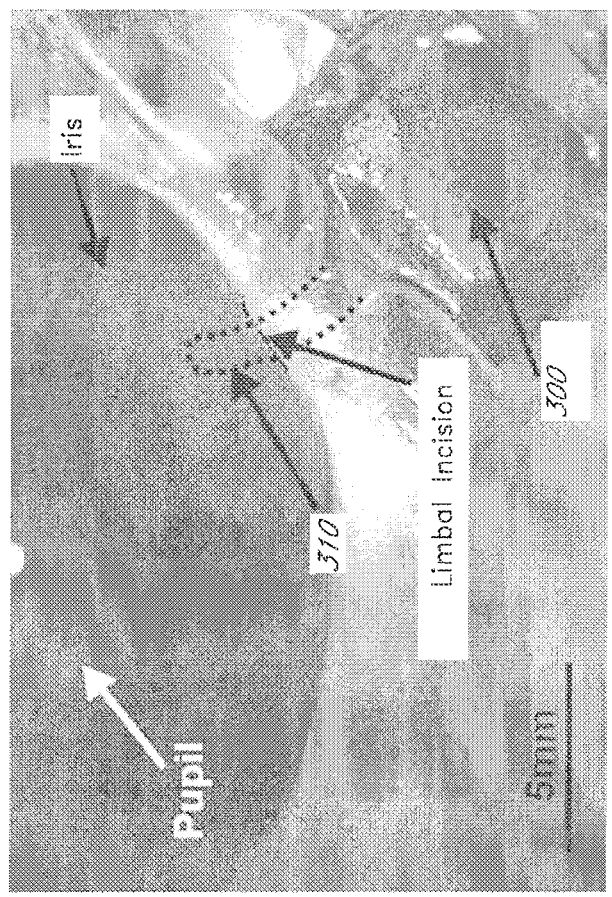
FIG. 20 illustrates ex vivo testing of the device in a porcine eye showing the electrolysis driven delivery of dyed DI water into the anterior chamber.

The prototype drug delivery devices were implanted in enucleated porcine eyes. Preliminary ex vivo surgical modeling in enucleated porcine eyes is useful to prepare for device demonstration in vivo. The operation of each surgical device was tested prior to the surgical experiment to check for clogs and integrity of the electrical connections. The drug reservoir was filled with dyed deionized water then the reservoirs were manually depressed which generates sufficient pressure to expel the fluid from the reservoir. A second, test is conducted to verify operation of the electrolysis pump by connecting to an external power supply and driving fluid from the reservoir by electrolysis pumping. An enucleated porcine eye was prepared, for the surgical study and a limbal incision was made (between the cornea and sclera). The cannula was implanted through the incision into the anterior chamber (FIG. 20). The enucleated porcine eye was pressurized at 15 mmHg by using an infusion line. Constant current (0.5 mA) was applied for 1 minute. The device was surgically removed after the experiment.

Figure 21A:
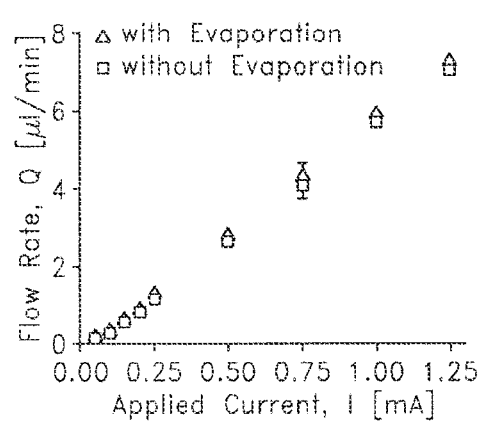
FIG. 21A illustrates current-controlled flow delivery after evaporation compensation (mean±SE, n=4) with the calibrated water evaporation rate in the micro-pipette of about 30 nL/min for example devices implanted in enucleated porcine eyes.
Figure 21B:
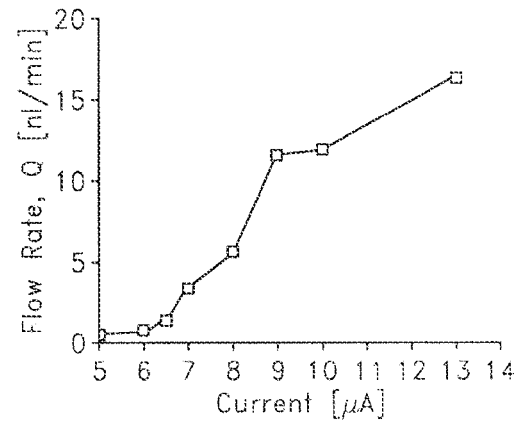
FIG. 21B illustrates low flow rate operation of the example devices of FIG. 21A.
Figure 21C:
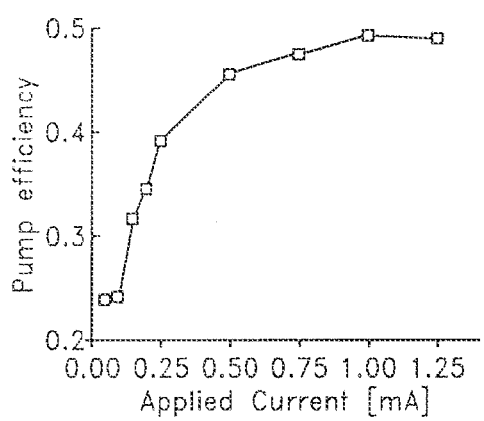
FIG. 21C illustrates pump efficiency calculated from flow delivery data for the example devices of FIG. 21A.
Figure 21D:
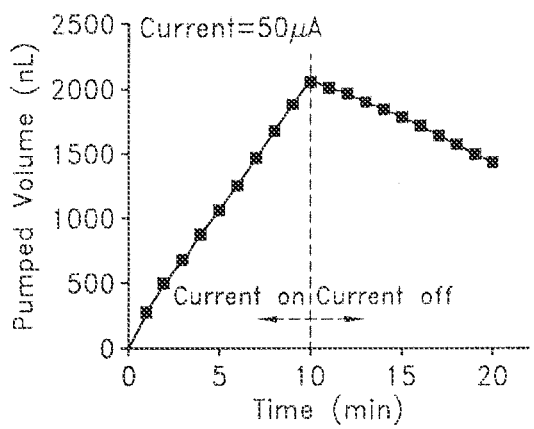
FIG. 21D illustrates typical gas recombination observed in the example devices of FIG. 21A. 50 microamp current was applied for 10 minutes and then turned off.

The electrolysis pump was operated at flow rates in the pL/min to µL/min range using driving currents from 5 µA to 1.25 mA (FIGS. 21A and 21B). The highest rate was 7 µL/min for 1.25 mA and the lowest was 438 pL/min at 5 µA. Both data sets am corrected to compensate for the evaporation of fluid during testing. Flow rates below about 2 µL/min are preferred for ocular drug delivery. This is consistent with naturally occurring flow sates in the eye; the ciliary body of the eye produces aqueous humor at 2.4±0.6 µL/min in adults. As current decreases, it was observed that pumping efficiency, which ranged from 24-49%, also decreased (FIG. 21C) Electrolysis-driven pumping efficiency is affected by the competitive recombination of hydrogen and oxygen gases to water. This effect is further enhanced by exposure to the platinum electrolysis electrodes which serve to catalyze the recombination reaction. In FIG. 21D, a typical accumulated volume curve is shown that illustrates the effect of recombination after the applied current is turned off. The measured recombination rate was 62 nL/min.

Figure 22:
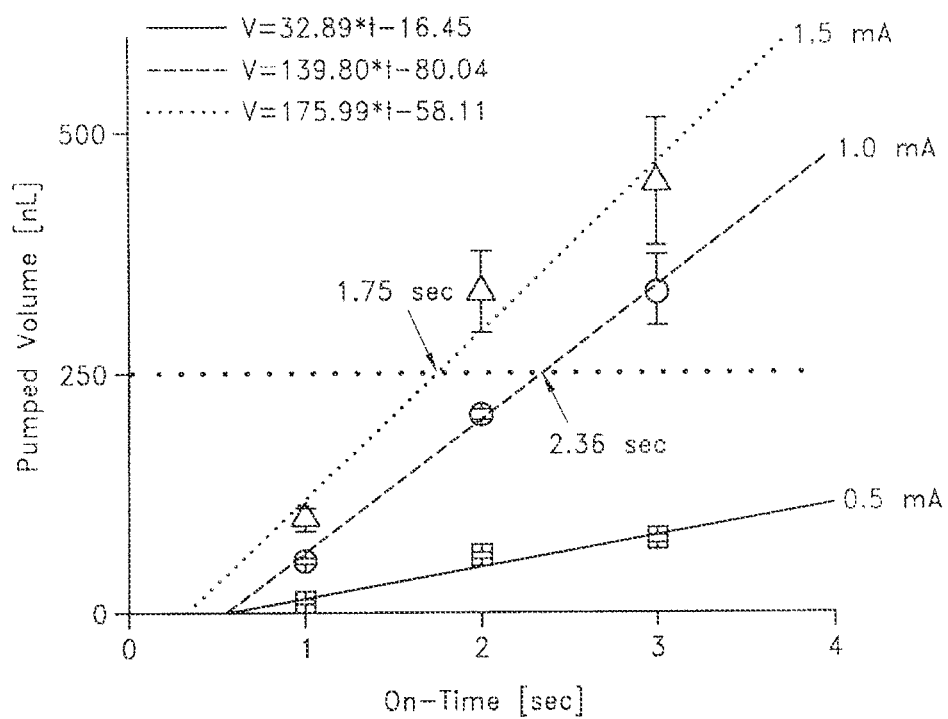
FIG. 22 illustrates bolus delivery of 250 nL doses using current pulses.
Figure 23:
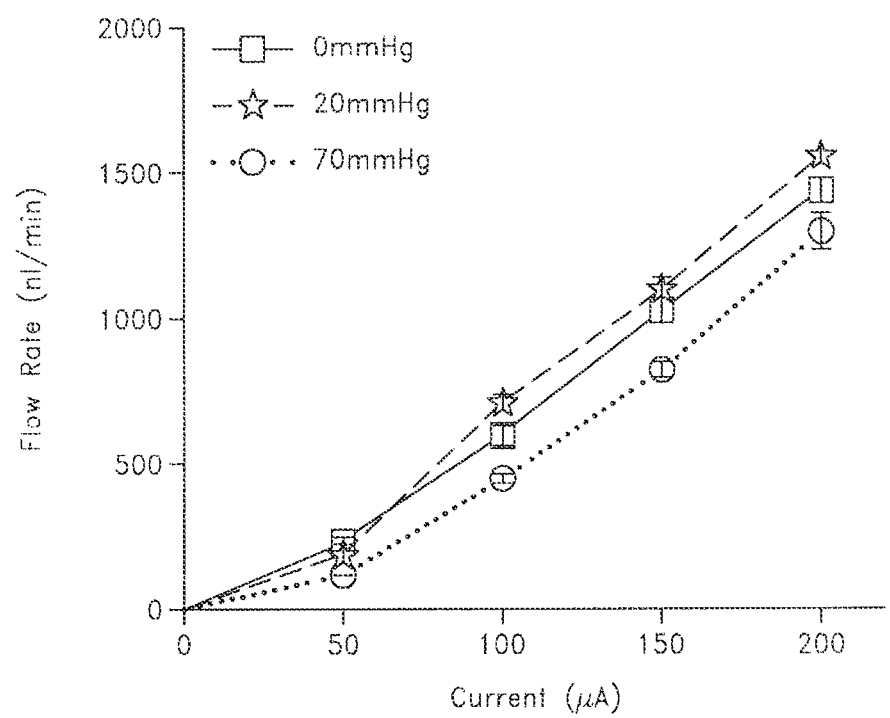
FIG. 23 illustrates now performance under physiological back pressures (mean±SE, n=4).

Bolus delivery mode is also evaluated (FIG. 22). If the desired dosing regimen is 250 nL per dose, this volume can be obtained by driving the pump for a short duration that is determined by the magnitude of the applied current. For example, a 1.0 mA driving current will dose 250 nL in 2.36 second and, for 1.5 mA current, the pulse time can be set as 1.75 second. Under normal operation in the eye, the drug delivery device will experience a backpressure equivalent to the IOP of the eye. Benchtop experiments indicated that the pump was able to supply sufficient drug flow over the range of normal and abnormal IOP equivalent backpressures (FIG. 23). The flow rates varied 30% compared to normal IOP over the tested backpressure range.

Initial surgical results show promising results in enucleated porcine eyes. Following removal of the device after the surgical experiment, post surgical examination of the cornea revealed a small blue spot above the iris near the position of the cannula tip indicating that dye was delivered into the eye.

The above description is by way of illustration only and is not intended to be limiting in any respect. While the above detailed description has described features of the invention as applied to various embodiments, the scope of the invention is indicated by the appended claims rather than by the foregoing description.

What is claimed is:

1. A method of manufacturing an implantable pump, the method comprising:
   providing an upper layer comprising a dome structure for housing a drug chamber and a cannula in fluid communication with the drug chamber;
   providing a middle deflection layer adjacent the drug chamber;
   providing a bottom layer comprising electrolysis electrodes; and
   bonding the upper layer, middle deflection layer, and bottom layer along a common peripheral exterior edge of the upper and middle deflection layers to form the pump.

2. The method of claim 1, further comprising the step of forming the drug chamber between the upper layer and the middle deflection layer after thermal bonding.

3. The method of claim 1, further comprising the step of forming the electrolysis chamber between the middle deflection layer and the bottom layer after thermal bonding.

4. The method of claim 1, further comprising providing at least one fill port in fluid communication with at least one of the electrolysis chamber or the drug chamber.

5. The method of claim 1, wherein at least one of the upper layer, the middle layer, and the bottom layer is formed by a lithographic process.

6. The method of claim 5, wherein the lithographic process comprises the steps of:
   sequentially layering layers of a construction material and a photoresist material;
   etching at least one of the construction material and a photoresist material to provide a required shape, and
   subjecting the layers to photoresist stripper, thereby removing the photoresist material and leaving the shaped construction material in place.

7. The method of claim 1, wherein at least one of the upper layer, the middle layer, and the bottom layer is formed by a molding process.

8. The method of claim 1, wherein at least one of the upper layer, the middle layer, and the bottom layer comprises or consists essentially of parylene.

9. The method of claim 1, wherein the dome structure is manufactured by the steps of:
   providing a mold having a domed shape;
   conformably coating a layer of material on the mold; and
   after the material has set, peeling the resulting dome structure from the mold.

10. The method of claim 1, wherein the cannula is manufactured according to steps comprising:
    coating a first photoresist layer onto a silicon substrate as a sacrificial layer;
    depositing a first parylene layer onto the photoresist layer to form a bottom surface of the cannula;
    creating a through hole in the first parylene layer;
    coating a second photoresist layer over the first parylene layer;
    depositing a second parylene layer on the second photoresist layer, the second parylene layer forming a top and a side of the cannula;
    patterning the first and second parylene layers to form a cannula shape; and
    removing the first and second photoresist layers, thereby leaving the formed cannula.

11. The method of claim 10, wherein the patterning step comprises reactive-ion etching with a photoresist material used as an etching mask.

12. The method of claim 10, wherein the patterning step comprises patterning the first parylene layer and second parylene layer in a RIE oxygen plasma using a photoresist mask.

13. The method of claim 10, wherein at least one of the coating steps comprises spin-coating.

14. The method of claim 1, further comprising integrating at least one of a check valve, a flow sensor, a pressure sensor, or a chemical sensor into the pump.

15. The method of claim 11, wherein the middle deflection layer comprises a corrugated diaphragm.

16. The method of claim 15, wherein the corrugated diaphragm is formed according to steps comprising:
    coating a first photoresist layer onto a silicon substrate;
    etching the silicon substrate using the first photoresist layer as a mask;
    removing the first photoresist layer, thereby leaving a mold formed by the silicon substrate;
    coating a parylene layer on the silicon substrate; and
    after the parylene layer has set, releasing the parylene layer from the silicon substrate thereby forming the corrugated diaphragm.

17. The method of claim 1, wherein the middle deflection layer comprises a bellows structure.

18. The method of claim 17, wherein the bellows structure is formed according to steps comprising:
    coating a first photoresist layer onto a silicon substrate as a sacrificial layer;
    depositing a first parylene layer onto the first photoresist layer to form a first layer of the bellows structure;
    coating a second photoresist layer over the first parylene layer;
    opening a bonding area in the second photoresist layer by lithography;
    depositing a second parylene layer onto the second photoresist layer to form a second layer of the bellows structure, wherein the second parylene layer bonds to the first parylene layer at the bonding area;
    patterning the first and second parylene layers;
    coating a third photoresist layer onto the second parylene layer;

depositing a third parylene layer onto the third photoresist layer to form a third layer of the bellows structure;

patterning the bellows structure by etching through the second and third parylene layers; and removing the photoresist layers by subjection to photoresist stripper, thereby leaving the parylene bellows structure.

19. The method of claim 1, wherein the bottom layer is formed according to steps comprising:

coating a first photoresist layer onto a silicon substrate as a sacrificial layer;

depositing a first parylene layer onto the first photoresist layer to form a first layer of the bottom layer;

depositing a metal electrode layer on the first parylene layer;

depositing a second parylene layer over the metal electrode layer;

etching the second parylene layers to expose at least a portion of the electrode; and removing the photoresist layers by subjection to photoresist stripper, thereby leaving the bottom layer.

20. The method of claim 19, wherein the metal electrode layer is deposited by E-beam evaporation and patterned by life-off process or etching process.

21. The method of claim 19, wherein the etching step comprises RIE oxygen plasma etching masked by a photoresist mask.

22. The method of claim 19, further comprising annealing the bottom layer to improve the adhesion between the parylene layers and metal electrode layer.

23. The method of claim 19, wherein the metal electrode layer comprises or consists essentially of platinum.

24. The method of claim 1, further comprising a substantially rigid spacer comprising a refill hole.

* * * * *